US006410690B1

(12) United States Patent
Deo et al.

(10) Patent No.: US 6,410,690 B1
(45) Date of Patent: *Jun. 25, 2002

(54) THERAPEUTIC COMPOUNDS COMPRISED OF ANTI-FC RECEPTOR ANTIBODIES

(75) Inventors: Yashwant M. Deo, Audubon, PA (US); Joel Goldstein, Piscataway; Robert Graziano, Frenchtown, both of NJ (US); Chezian Somasundaram, Allentown, PA (US)

(73) Assignee: Medarex, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/484,172

(22) Filed: Jun. 7, 1995

(51) Int. Cl.[7] .................. C12P 21/08; C07K 16/06; C07K 16/18; C07K 16/28
(52) U.S. Cl. .................. 530/387.3; 530/387.7; 530/388.15; 530/388.22; 530/388.8; 530/388.85
(58) Field of Search ............... 530/387.1, 387.3; 424/136.1, 133.1, 134.1, 137.1, 139.1, 141.1, 143.1, 152.1, 153.1, 155.1, 156.1; 514/12

(56) References Cited

U.S. PATENT DOCUMENTS

| 4,753,894 A | * | 6/1988 | Frankel et al. |
| 4,943,533 A | * | 7/1990 | Mendelsohn et al. |
| 4,954,617 A | * | 9/1990 | Fanger et al. |
| 5,084,396 A | * | 1/1992 | Morgan, Jr. et al. |
| 5,288,477 A | * | 2/1994 | Bacus |
| 5,558,864 A | * | 9/1996 | Bendig et al. |
| 5,597,569 A | * | 1/1997 | Siegall et al. |

FOREIGN PATENT DOCUMENTS

| WO | 9100360 | * | 1/1991 | |
| WO | WO 91 05871 | | 5/1991 | |
| WO | WO 91/03493 | | 3/1992 | ........... C07K/15/28 |
| WO | WO 92 05793 | | 4/1992 | |
| WO | WO 94/10332 | | 5/1994 | ........... C12P/21/08 |
| WO | WO 95/09917 | | 4/1995 | ........... C12N/15/13 |

OTHER PUBLICATIONS

Jawetz et al (Medical Microbiology 19th edition San Mateo, CA 1991 p. 115).*
Jung, Gundram, et al., (1991), "Target Cell–Induced T cell Activation with Bi– and Trispecific Antibody Fragments", *Eur. J. Immunol.*, vol. 21, pp. 2431–2435.
Fanger, M. et al. (1994) "Production and Use Of Anti–FcR Bispecific Antibodies" *Immunomethods* 4 (1): 72–81.
Repp, R. et al. (1994) "G–CSF Stimulated Neutrophils As Effector Cells In Immunotherapy With A Bispecific Antibody to FcgammaRI and To HER–2/neu (MDX210): Preclinical Studies", *Immunobiology*, 191 (2–3): 250–251.
Mabondzo, A. et al. (1994) "Antibody–Dependent Cellular Cytotoxicity and Neutralization of Human Immunodeficiency Virus Type 1 By High Affinity Cross–Linking of gp41 to Human Macrophage Fc IgG Receptor Using Bispecific Antibody" *Journal of General Virology*, 75 (6): 1451–1456.
Chen, J. et al. (1995) "An Immunoconjugate of Lys3–Bombesin and Monoclonal Antibody 22 Can Specifically INduce FcgammaRI (CD64)–Dependent Monocyte– and Neutrophil–Mediated Lysis of Small Cell Carcinoma of the Lung Cells" *Clinical Cancer Reseach*, 1 (4): 425–434.

* cited by examiner

*Primary Examiner*—Geetha P. Bansal
(74) *Attorney, Agent, or Firm*—Lahive & Cockfield, LLP; Jane E. Remillard; Peter W. Dini

(57) ABSTRACT

Multispecific multivalent molecules which are specific to an Fc receptor (FcR), and therapeutic uses and therapeutic uses and methods for making the molecules are described.

17 Claims, 12 Drawing Sheets h22 HINGE REGION:

[A]

-ACT CAC ACA TGC CCA CCG TGC CCA —— CH2 —— CH3   SEQ ID NO:1
 T   H   T   C   P   P   C   P

[B]
```
                              —BamHI—
-ACT CAC ACA TGC CCA CCG TGA GGA TCC-
 T   H   T   C   P   P   *
```

[C]
```
                 —XhoI—         —NotI—          —BamHI—
-ACT CAC ACA TGC TCG AGC CTT CAC GGC GGC CGC TGA GGA TCC
 T   H   T   C   S   S   L   H   G   G   R   *
```

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..24

(xi) SEQUENCE DESCRIPTION: SEQ ID NO:1:

ACT CAC ACA TGC CCA CCG TGC CCA                                          24
Thr His Thr Cys Pro Pro Cys Pro
  1               5

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..19

(xi) SEQUENCE DESCRIPTION: SEQ ID NO:2:

ACT CAC ACA TGC CCA CCG T GAGGATCC                                       27
Thr His Thr Cys Pro Pro
  1               5

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..34

(xi) SEQUENCE DESCRIPTION: SEQ ID NO:3:

ACT CAC ACA TGC TCG AGC CTT CAC GGC GGC CGC T GAGGATCC                   42
Thr His Thr Cys Ser Ser Leu His Gly Gly Arg
  1               5                  10
```

US 6,410,690 B1

THERAPEUTIC COMPOUNDS COMPRISED OF ANTI-FC RECEPTOR ANTIBODIES

BACKGROUND OF THE INVENTION

Immunoglobulins (Igs) are composed of two heavy and two light chains, each of which contains an $NH_2$-terminal antigen-binding variable domain and a COOH-terminal constant domain responsible for the effector functions of antibodies. The COOH-terminal domains of Ig heavy chains form the Fc region and are involved in triggering cellular activities through interaction with specific receptors known as Fc receptors (FcRs). Fc receptors for all Ig classes, or isotypes, (e.g., IgG (FcγR), IgE (FcεR), IgA (FcαR), IgM (FcμR) and IgD (FcδR) have been identified. The different biological activities of antibodies of different isotypes are based in part on their ability to bind to different FcR expressed on different immune (effector) cells (Fridman, W. H. (September 1991) The FASEB Journal Vol. 5. 2684–2690). Murine antibodies, which are directed against FcRs have been made (See e.g. U.S. Pat. No. 4,954,617 entitled *Monoclonal Antibodies To Fc Receptors for Immunoglobulin G on Human Mononuclear Phagocytes* and International Patent Application Publication No. WO 91/05871 entitled *Monoclonal Antibody Specific For IgA Receptor*).

Murine monoclonal antibodies can be useful as human therapeutics and can be produced free of contamination by human pathogens such as the hepatitis or human immunodeficiency virus. However, use of murine monoclonal antibodies in some human therapies, have resulted in the development of an immune response to the "foreign" murine proteins. This response has been termed a human anti-mouse antibody or HAMA response (Schroff, R. et al. (1985), *Cancer Res.*, 45, 879–885) and is a condition which causes serum sickness in humans and results in rapid clearance of the murine antibodies from an individual's circulation. The immune response in humans has been shown to be against both the variable and the constant regions of murine immunoglobulins.

Recombinant DNA technology can be used to alter antibodies, for example, by substituting specific immunoglobulin regions from one species with immunoglobulin regions from another species. Neuberger et al. (Patent Cooperation Treaty Patent Application No. PCT/GB85/00392) describes a process whereby the complementary heavy and light chain variable domains of an Ig molecule from one species may be combined with the complementary heavy and light chain Ig constant domains from another species. This process may be used to substitute the murine constant region domains to create a "chimeric" antibody which may be used for human therapy. A chimeric antibody produced as described by Neuberger et al. has a human Fc region for efficient stimulation of antibody mediated effector functions, such as complement fixation, but still has the potential to elicit an immune response in humans against the murine ("foreign") variable regions.

Winter (British Patent Application Number GB2188538A) describes a process for altering antibodies by substituting the complementarity determining regions (CDRs) with those from another species. This process may be used to substitute the CDRs from the murine variable region domains of a monoclonal antibody with desirable binding properties (for instance to a human pathogen) into human heavy and light chain Ig variable region domains. These altered Ig variable regions may then be combined with human Ig constant regions to create antibodies which are totally human in composition except for the substituted murine CDRs. The "reshaped" or "humanized" antibodies described by Winter elicit a considerably reduced immune response in humans compared to chimeric antibodies because of the considerably less murine components. Further, the half life of the altered antibodies in circulation should approach that of natural human antibodies. However, as stated by Winter, merely replacing the CDRs with complementary CDRs from another antibody which is specific for an antigen such as a viral or bacterial protein, does not always result in an altered antibody which retains the desired binding capacity. In practice, some amino acids in the framework of the antibody variable region interact with the amino acid residues that make up the CDRs so that amino acid substitutions into the human Ig variable regions are likely to be required to restore antigen binding.

Bispecific molecules, (e.g., heteroantibodies) comprising an anti-Fc receptor portion and an anti-target portion have been formulated and used therapeutically, e.g., for treating cancer (e.g. breast or ovarian) or pathogenic infections (e.g., HIV) (See, e.g., International Patent Application Publication No. WO 91/05871 entitled *Bispecific Heteroantibodies With Dual Effector Functions;* and International Patent Application Publication No. WO 91/00360 entitled *Bispecific Reagents for AIDS Therapy*). In addition, bispecific molecules, which recognize antigens and antigen presenting cells can be administered to a subject to stimulate an immune response (See, e.g., International Patent Application Publication No. WO 92/05793 entitled *Targeted Immunostimulation With Bispecific Reagents*).

SUMMARY OF THE INVENTION

In one aspect, the invention features multispecific, multivalent molecules, which minimally comprise an anti-Fc receptor portion, an anti-target portion and optionally an anti-enhancement factor (anti-EF) portion. In preferred embodiments, the anti-Fc receptor portion is an antibody fragment (e.g., Fab or (Fab')₂ fragment), the anti-target portion is a ligand or antibody fragment and the anti-EF portion is an antibody directed against a surface protein involved in cytotoxic activity. In a particularly preferred embodiment, the recombinant anti-FcR antibodies, or fragments are "humanized" (e.g., have at least a portion of a complementarity determining region (CDR) derived from a non-human antibody (e.g., murine) with the remaining portion(s) being human in origin).

In another aspect, the invention features methods for generating multispecific molecules. In one embodiment, both specificities are encoded in the same vector and are expressed and assembled in a host cell. In another embodiment, each specificity is generated recombinantly and the resulting proteins or peptides are conjugated to one another via sulfhydryl bonding of the C-terminus hinge regions of the heavy chain. In a particularly preferred embodiment, the hinge region is modified to contain only one sulfhydryl residue, prior to conjugation.

Recombinant antibodies and multispecific molecules generated therefrom can be engineered to have increased affinity and specificity. Further, humanized antibodies are typically less immunogenic when administered to a human. Other features and advantages of the present invention will become better understood by reference to the following Detailed Description and Claims.

DETAILED DESCRIPTION

Multispecific Molecules

Figure 1:
FIG. 1 is a diagram showing the nucleotide and amino acid residue sequences of a portion of the hinge region of a humanized Fcγ RI antibody, H22' [A] that was altered to produce a truncated single-sulfhydryl version [B] and then altered further to engineer two unique cloning sites [C]. Underlined nucleotides indicate changes from the previous sequence. Overlined nucleotides are the recognition sequences for the indicated restriction sites.
Figure 1:

The instant invention relates to recombinantly produced multispecific molecules. Multispecific molecules can include bispecific molecules comprised of an anti-Fc receptor portion and an anti-target portion, wherein at least one of said portions is constructed using recombinant DNA techniques. Multispecific molecules can also include molecules, which are comprised of more than one anti-Fc receptor portion or anti-target portion; or molecules comprised of at least one anti-Fc receptor, one anti-target portion and additionally a portion or portions that recognize another molecule, wherein at least one of said portions is constructed using recombinant DNA techniques.

An "anti-Fc receptor portion" refers to an antibody, a functional antibody fragment (e.g., Fab fragment) or a ligand that recognizes and binds an Fc receptor on an effector cell. Preferred antibodies for use in the subject invention bind the Fc receptor on an effector cell at a site which is not bound by endogenous immunoglobulin. Most preferably, the anti-Fc receptor portion binds a human FcγR (i.e., FcγRI, FcγRII or FcγRIII). Preferred humanized anti-FcγR monoclonal antibodies are described in PCT application WO 94/10332 and U.S. Pat. No. 4,954,617, the teachings of which are fully incorporated herein by reference.

An "effector cell", as used herein refers to an immune cell. Specific effector cells express specific Fc receptors and carry out specific immune functions. For example, monocytes, macrophages, neutrophils and dendritic cells, which express FcγRI are involved in both specific killing of target cells and presenting antigens to other components of the immune system. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI cells against targets.

The recombinant antibodies or antibody fragments, which specifically bind to an Fc receptor are preferably "humanized" i.e. derived from a human antibody, but having at least a portion of a complementarity determining region (CDR) derived from a non-human antibody. The portion being selected to provide specificity of the humanized antibody for a human Fc receptor. The humanized antibody has CDRs derived from a non-human antibody and the remaining portions of the antibody molecule are human.

The antibody may be whole, i.e. having heavy and light chains or any fragment thereof, e.g., Fab or (Fab')₂ fragment. The antibody further may be a light chain or heavy chain dimer, or any minimal fragment thereof such as a Fv or a single chain construct as described,in Ladner et al. (U.S. Pat. No. 4,946,778, issued Aug. 7, 1990), the contents of which are expressly incorporated by reference.

The humanized antibody or fragment may be any human antibody capable of retaining non-human CDRs. The preferred human antibody is derived from known proteins NEWM and KOL for heavy chain variable regions (VHs) and REI for Ig kappa chain, variable regions (VKs).

The portion of the non-human CDR inserted into the human antibody is selected to be sufficient for allowing binding of the humanized antibody to the Fc receptor. A sufficient portion may be selected by inserting a portion of the CDR into the human antibody and testing the binding capacity of the created humanized antibody using the enzyme linked immunosorbent assay (ELISA).

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor. A non-human CDR derived from a murine monoclonal antibody (mab), mab 22, is described in International Patent Application Publication No. WO 94/10332, the contents of which are fully incorporated herein by reference. The mab 22 antibody is specific to the Fc receptor and further is described in U.S. Pat. No. 4,954,617, issued Sep. 4, 1988, the contents of which are also expressly incorporated by reference. The humanized mab 22 antibody producing cell line was deposited at the American Type Culture Collection on Nov. 4, 1992 under the designation HA022CL1 and has the accession no. CRL 11177.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which are expressly incorporated by reference. The human CDRs may be replaced with non-human CDRs using oligonucleotide site-directed mutagenesis as described in International Patent Application Publication Number: WO 94/10332 entitled, *Humanized Antibodies to Fc Receptors for Immunoglobulin G on Human Mononuclear Phagocytes.*

In addition to an anti-Fc receptor portion, the claimed multispecific molecules can comprise an "anti-target portion", i.e. an antibody, a functional antibody fragment or a ligand that recognizes and binds a pathogen (e.g., virus, bacteria, fungi), a pathogen infected cell, a cancer or tumor cell (e.g., breast, ovarian, prostate, etc.) or other unwanted cell in a subject (e.g., a human or animal). Additionally, the anti-target portion may be directed against an antigen. A preferred embodiment contains an antigen that can be used to stimulate the immune system, for example, in instances of chronic infection, to deplete antigen in the circulation, and to treat tumors. A particularly preferred embodiment has an antigen that is attached to a multivalent molecule containing an anti-FcR antibody.

The multispecific, multivalent molecules of the invention may also include an "anti-enhancement factor (anti-EF) portion". The "anti-enhancement factor portion" can be an antibody, functional antibody fragment or a ligand that binds to an antigen and thereby results in an enhancement of the effect of the anti-$F_c$ receptor portion or the anti-target portion. The "anti-enhancement factor portion" can bind an $F_c$ receptor or a target. A multivalent molecule comprising an anti-target portion that binds to one target cell antigen and an anti-enhancement factor portion that binds to a different target antigen is particularly useful where the target cell undergoes antigen modulation or antigenic variation (e.g., as has been described for certain parasites (such as trypanosomes). Alternatively, the anti-enhancement factor portion can bind an entity that is different from the entity to which the anti-target or anti-$F_c$ receptor portion binds. For example, the anti-enhancement factor portion can bind a cytotoxic T-cell (e.g. via CD2, CD3, CD8, CD28, CD4, CD40, ICAM-1) or other immune cell that results in an increased immune response against the target.

Methods for Making Multispecific Molecules

The multispecific molecules described above can be made by a number of methods. For example, each specificity can be encoded in the same vector and expressed and assembled in the same host cell. This method is particularly useful where the multi-specific molecule is a ligand×Fab fusion protein as described in the following Example 2.

Alternatively, each specificity of a multispecific molecule can be generated separately and the resulting proteins or peptides conjugated to one another. For example, two humanized antibodies can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

The bispecific molecules of the present invention can be prepared by conjugating the anti-FcR and anti-target portions using methods described in the following Example or those well-known in the art. For example, a variety of coupling or cross-linking agents can be used for covalent conjugation. Examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, MA et al. (1985) Proc. Natl. Acad. Sci. USA 82:8648). Other methods include those described by Paulus (Behring Ins. Mitt. (1985) No. 78, 118–132); Brennan et al. (Science (1985) 229:81–83), and Glennie et al. (J. Immunol. (1987) 139: 2367–2375). Preferred conjugating agents are SATA and sulfo-SMCC, both available from Pierce Chemical Co. (Rockford, Ill.).

Therapeutic Uses for Multispecific Molecules

Based on their ability to bind FcR bearing immune cells and specific target cells, a specific multispecific molecule can be administered to a subject to treat or prevent a variety of diseases or conditions, including: cancer (e.g., breast, ovarian, small cell carcinoma of the lung), pathogenic infections (e.g., viral (such as HIV)), protozoan (such as *Toxoplasma gondii*), fungal (such as *candidiasis*); an autoimmunity (e.g. immune thrombocytopenia purpura and systemic lupus). The multispecific multivalent can also be administered prophylactically to vaccinate a subject against infection by a target cell.

For use in therapy, an effective amount of an appropriate multispecific molecule can be administered to a subject by any mode that allows the molecules to exert their intended therapeutic effect. Preferred routes of administration include oral and transdermal (e.g., via a patch). Examples of other routes of administration include injection (subcutaneous, intravenous, parenteral, intraperitoneal, intrathecal, etc.). The injection can be in a bolus or a continuous infusion.

A multispecific molecule can be administered in conjunction with a pharmaceutically acceptable carrier. As used herein, the phrase "pharmaceutically acceptable carrier" is intended to include substances that can be coadministered with a multispecific molecule and allows the molecule to perform its intended function. Examples of such carriers include solutions, solvents, dispersion media, delay agents, emulsions and the like. The use of such media for pharmaceutically active substances are well known in the art. Any other conventional carrier suitable for use with the molecules falls within the scope of the instant invention.

The language "effective amount" of a multispecific molecules refers to that amount necessary or sufficient to realize a desired biologic effect. For example, an effective amount of a multi specific molecule, in which the anti-target portion recognizes a pathogenic cell could be that amount necessary to eliminate a tumor, cancer, or bacterial, viral or fungal infection. The effective amount for any particular application can vary depending on such factors as the disease or condition being treated, the particular multispecific molecule being administered, the size of the subject, or the severity of the disease or condition. One of ordinary skill in the art can empirically determine the effective amount of a particular multispecific molecule without necessitating undue experimentation.

The following examples are provided as a further illustration of the present invention and should in no way be construed as being limiting.

EXAMPLES

Example 1

Production of Bispecific Antibody Comprising Murine or Humanized Antibodies Specific for an Fc Receptor and an Anti-Her 2 neu Antibody Monoclonal Antibodies The anti-FcγRI monoclonal antibodies (mAbs), M22, M32.2 and 197 were purified from hybridoma supernatant by ion exchange chromatography and DZ33, a human anti-HIV-1 IgG1 mAb, was purified from hybridoma supernatant by protein A affinity chromatography (Pharmacia, Piscataway, N.J.) and gel filtration. M32.2 was deposited at the American Type Culture Collection, 12301 Parklawn Drive, Rockville, Md. 20852, on Jul. 1, 1987 and has been designated with ATCC Accession No. HB9469.

Cell Lines

The murine myeloma NSO (ECACC 85110503) is a non-Ig synthesizing line and was used for the expression of recombinant mAbs. NSO cells were cultivated in DMEM plus 10% fetal bovine serum (FBS, Gibco, Paisley, U.K.). SKBR-3 is a human breast carcinoma cell line which overexpresses the HER2/neu protooncogene (ATCC, Rockville, Md.) and was cultivated in Iscove's Modified Dulbecco's Medium (IMDM, Gibco, Grand Island, N.Y.). U937 is a monocytoid cell line that expresses FcγRI and was obtained from ATCC and grown in RPM-1640 plus 10% FBS (Gibco, Grand Island, N.Y.).

Cloning Murine Immunoglobulin V Region Genes

Cytoplasmic RNA from the murine hybridoma 22 was prepared as described in Favaloro et al. (Favaloro, J., R. Treisman and R. Kamen (1982) Transcription maps of polyoma-specific RNA: analysis by two-dimensional S1 gel mapping. *Meth. Enzymol.* 6:718). The Ig V region cDNAs were made from RNA via reverse transcription initiated from primers CG1FOR and CK2FOR as described in International Patent Application Publication Number WO 94/10332 entitled, *Humanized Antibodies to Fc Receptors for Immunoglobulin G on Human Mononuclear Phagocytes.* The cDNA synthesis was performed under standard conditions using 100 U MMLV reverse transcriptase (Life Technologies, Paisley, UK). The $V_H$ and $V_\kappa$ cDNAs were amplified by PCR, (Orlandi, R., D. H. Güssow, P. T. Jones and G. Winter (1989) (Cloning immunoglobulin variable domains for expression by the polymerase chain reaction), *Proc. Natl. Acad. Sci. USA* 863833), using the cDNA primers in concert with SH2BACK and VK7BACK as described in International Patent Application Publication Number WO 94/10332. Amplified $V_H$ and $V_\kappa$ DNA were purified, cloned into M13, and sequenced by the dideoxy method using T7 DNA polymerase (Pharmacia, Piscataway, N.J.).

Construction Of Chimeric Antibody Genes

To facilitate cloning of murine V region DNA into expression vectors, restriction sites were placed in close proximity to the termini of both M22 V region genes. For $V_H$, a 5' PstI site and a 3' BstEII site were introduced into a cloned murine $V_H$ gene by PCR using VH1BACK and VH1FOR (Id.). For $V_\kappa$ a 5' PvuII site and a 3' Bgl II site were introduced into a cloned murine $V_\kappa$ gene by PCR using primers VK1BACK and VK1FOR (Id.). In some instances, these primers changed one or more amino acids from those naturally occurring. These V region genes (ChVH and ChVK) were cut with the appropriate restriction enzymes and cloned into M13VHPCR1 and M13VKPCR1 (Id.) which contain an Ig promoter, signal sequence and splice sites. The DNA were excised from M13 as HindIII-BamHI fragments and cloned into the expression vectors pSVgpt and pSVhyg containing human IgG1, (Takahashi, N. et al., (1982), Structure of human immunoglobulin gamma genes: implications for evolution of a gene family, *Cell,* 22:671), and human kappa constant, (Hieter, R. A. et al., (1980) Cloned human and mouse kappa immunoglobulin constant and J region genes conserve homology in functional segments, *Cell* 22:197), region genomic DNA.

Construction of Humanized Antibody Genes

Two humanized heavy chains were constructed and were based on human $V_H$s of NEWM, (Poljak, R. J. et al., Amino acid sequence of the $V_H$ region of a human myeloma immunoglobulin, (IgG New), *Biochemistry,* 16:3412), and KOL,(Marquat, M. et al., (1980) Crystallographic refinement and atomic models of the intact immunoglobulin molecule Kol and its antigen-binding fragment at 3.0A and 1.9A resolution, *J. Mol. Biol* 141:369). The humanized light chain was derived from the human Bence-Jones protein REI, (Epp, O. et al, (1974) Crystal and molecular structure of a dimer composed of the vandible portion of the Bence-Jones protein REI, *Eur. J. Biochem.* 45:513), with some framework region (FR) changes. The modifications were made to make the Vκ domain more typical of human subgroup I, and included replacement of Thr39, Leu104, Gln105 and Thr107 with Lys39, Val104, Glu105 and Lys107. In addition, Met4 was changed to Leu4 to accommodate a PvuII restriction site.

DNA containing the NEWM $V_H$ and REI $V_\kappa$ FRs with irrelevant CDRs were cloned into the vectors M13VHPCR1 and M13VKPCR1 (Favaloro et al. Supra). DNA encoding the KOL $V_H$ was constructed by a series of sequential PCRs, using oligodeoxyribonucleotides encoding KOL FR amino acids and irrelevant CDRs. The constructs were then cloned into M13VHPCR1.

Oligodeoxyribonucleotides were synthesized to encode the mAB M22 CDRs which were flanked by nucleotides corresponding to the human FRs. For the humanized $V_H$ based on NEWM, the primers included murine FR amino acids Phe27, Ile28 and Arg71 since these were likely to influence antigen binding, (Chothia, C. and A. M. Lesk (1987), Canonical structures for the hypervariable regions of immunoglobulins, *J. Mol. Biol,* 196:90 1; Tramontano, A. et al., (1990), Framework residue 71 is a major determinant of the position and conformation of the second hypervariable region in $V_H$ domains of immunoglobulins, *J. Mol. Biol.,* 215:175). For the humanized $V_\kappa$, murine amino acid Phe71 was similarly included as a residue capable of affecting affinity, (Foote, J. and G. Winter, (1992), Antibody framework residues affecting the conformation of the hypervariable loops, *J. Mol Biol.* 224:487). No murine FR residues were included in the KOL $V_H$. Oligodeoxyribonucleotides were 5'-phosphorylated and with the M13 universal forward primer annealed to the human V region genes cloned in M13 in reactions containing M13 ssDNA template. The DNA was extended and ligated with 2.5 U T7 DNA polymerase (United States Biochemicals, Cleveland, Ohio) and 0.5 U T4 DNA ligase (Gibco BRL, Grand Island, N.Y.). The mutated strand was preferentially amplified from the extension/ligation mixture using M13 reverse sequencing primer with 1 U Vent DNA polymerase (New England Biolabs, Beverly, Mass.) and was then amplified by PCR using both M13 forward and reverse primers. Product DNA was cut with BamH1 and HindIII, cloned into M13 and triple CDR-grafted mutants identified by DNA sequencing.

M13 clones containing the humanized V regions were sequenced in their entirety to ensure the absence of spurious mutations. RF DNA from the confirmed clones was digested with HindIII and BamHI, cloned into pSVgpt or pSVhyg and human IgG1 or human kappa constant regions added exactly as described for the construction of the chimeric antibody genes.

Expression and Purification of Recombinant mAbs

Heavy (5 μg) and light (10 μg) chain expression vectors were digested with PvuI, ethanol precipitated and dissolved in 50 μl water. NSO cells (1–2×10$^7$) were harvested by centrifugation, resuspended in 0.5 ml DMEM and mixed with the DNA in a 0.4 cm electroporation cuvette. After 5 min. on ice the cells were given a single pulse of 170 V, 960 μF (GenePulser, Bio-Rad, Melville, N.Y.) and incubated further for 15 min. on ice. The cells were allowed to recover in DMEM for 24–48 hours. The medium was then made selective by the addition of mycophenolic acid (0.8 ug/ml) and xanthine (250 μg/ml). Aliquots of 200 μl were distributed into 96-well plates. After a further 10–12 days, cells from the wells containing the highest levels of antibody measured by ELISA were selected and cloned by limiting dilution.

Antibodies were purified from overgrown cultures by protein A affinity chromatography (Boehringer Mannheim, Lewes, U.K.) Concentrations were determined by measuring $A_{280\ nm}$ and confirmed by ELISA and SDS-PAGE.

ELISA for Measurement of Antibody Binding

The wells of a microtiter plate were coated with goat anti-human IgM antibodies (Sera-Lab, Crawley Down, U.K.) in 50 mM bicarbonate buffer, pH 9.6. The plate was blocked with 1% BSA and followed by the addition of a soluble fusion protein consisting of the extracellular domain of human FcγRI and human IgM heavy chain (sFcγRI-μ) obtained from transiently transfected COS cells (the expression vector was kindly provided by Dr. Brian Seed, Massachusetts General Hospital, Boston, Mass.). Recombinant 22 or control mAbs were then added in the presence of excess (2.2 μg/well) human IgG1 antibodies (Sigma, St. Louis, Mo.) that contained λ light chains to block the non-specific binding of the test mAbs via their Fc portion. Bound 22 mAbs were detected with peroxidase-labeled goat anti-human kappa chain antibodies (Sera-Lab, Crawley Down, U.K.) and o-phenylenediamine.

Fluoresceination of Antibodies

The pH of mAb solution was adjusted to 9.3 by the addition of 0.1 M $Na_2CO_3$. Fluorescein iso-thiocyanate (FITC) (Sigma, St. Louis, Mo.) was dissolved in DMSO at a concentration of 2 mg/ml. Forty μg of FITC was added for each milligram of mAb and incubated for two hours at room temperature. The fluoresceinated mAb was separated from the free FITC by G-25 chromatography.

Preparation of Blood Cells

Buffy coats were prepared from heparinized whole venous blood. Whole blood was diluted with RPMI containing 5% dextran at a ratio of 2.5:1 (v/v). The erythrocytes were allowed to sediment for 45 minutes on ice, then the cells in the supernatant were transferred to a new tube and pelleted by centrifugation. The residual erythrocytes were removed by hypotonic lysis. The remaining lymphocytes, monocytes and neutrophils were kept on ice until use in binding assays. For some experiments, neutrophils were separated from mononuclear cells by ficoll hypaque (Pharmacia, Piscataway, N.J.) gradient separation. To up-regulate FcγRI, neutrophils and mononuclear cells were treated with cytokines. Cultures of mononuclear cells were incubated at 37° C., 5% $CO_2$ for 48 hours in teflon dishes at 4×10$^6$ cells/ml of RPMI containing 2.5% normal human serum type AB (Sigma, St. Louis, Mo.) and 500 IRU/ml IFN-γ (R&D Systems, Minneapolis, Minn.). Neutrophils were cultured for 48 hours (37° C., 5% $CO_2$) in AIM V media (Gibco, Grand Island, N.Y.) with 50 ng/ml G-CSF (Kindly provided by R. Repp, U. of Erlanger, Germany) and 500 IRU/ml IFN-γ.

Flow Cytometry

Cell binding assays were performed using 96-well microtiter plates as previously described, (Guyre, P. M. et al., Monoclonal antibodies that bind to distinct epitopes on FcγR are able to trigger receptor function. *J. Immunol.*, 143:1650). Briefly, cells were washed in PBS, pH 7.4 containing 2 mg/ml BSA and 0.05% $NaN_3$ (PBA), and adjusted to 2.0×10$^7$ cells/ml with PBA. FITC-labeled and unconjugated antibodies were prepared in PBA. Cells (25 μl), antibody (25 μl) and human serum (25 μl), or human IgG (10 mg/ml, Sigma, St. Louis, Mo.) (25 μl), or PBA (25 μl) were added to the microtiter plate, and left on ice for 45–60 minutes. Unbound antibody was removed from the wells by washing the cells 3 times with PBA. The cells were fixed with 1% paraformaldehyde. Cell associated fluorescence was analyzed on a Becton Dickinson FACScan.

BsAb Coupling Procedure

BsAb were constructed using the method of Glennie et al, (Glennie, M. J. et al., (1987), Preparation and performance of bispecific F(ab' gamma)$^2$, antibody containing thioether-linked Fab' gamma fragments, J. Immunol., 139:2367). mAbs 22 (both murine and humanized) and 520C9 (anti-HER2/neu) antibodies were produced by in vitro cultivation of the respective hybridoma cells. The hybridoma cell line producing monoclonal antibody 520C9 is available from American Type Culture Collection, ATCC Accession Number HB 8696. The antibodies were separately digested with pepsin to F(ab')$_2$, and subsequently reduced to Fab' by addition of 10 mM mercaptoethanolamine (MEA) for 30 minutes at 30° C. The Fab' fragments were applied to a Sephadex G-25 column equilibrated in 50 mM Na Acetate, 0.5 mM EDTA, pH 5.3 (4° C.). Ortho-phenylenedimaleimide (o-PDM, 12 mM) dissolved in dimethyl formamide and chilled in a methanol/ice bath was added (one half volume) to the murine 22 Fab' in the case of M 22×520C9, and to 520C9 Fab' in the case of H 22×520C9 and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the M22 Fab'- maleimide was added to the 520C9 Fab' or the 520C9 Fab'-maleimide was added to H22 Fab' at a 1:1 molar ratio. The reactants were concentrated under nitrogen to the starting volume using a Diaflo membrane in an Amicon chamber (all at 4° C.). After 18 hours the pH was adjusted to 8.0 with 1M Tris-HCl, pH 8.0. The mixture was then reduced with 10 mM MEA (30 minutes, 30° C.) Ads alkylated with 25 mM iodoacetamide. The bispecific F(ab')$_2$ was separated from unreacted Fab's and other products by a Superdex 200 (Pharmacia, Piscataway, N.J.) column equilibrated in PBS.

Antibody Dependent Cellular Cytotoxicity (ADCC)

The HER2/neu over-expressing human breast carcinoma cells, SKBR-3, were used as targets for lysis by cytokine activated neutrophils (see preparation of blood cells). Targets were labeled with 100 μCi of $^{51}$Cr for 1 hour prior to combining with neutrophils and antibodies in a U-bottom microtiter plate. After incubation for 5 hours at 37° C. supernatants were collected and analyzed for radioactivity. Cytotoxicity was calculated by the formula: % lysis= (experimental CPM—target leak CPM/detergent lysis CPM—target leak CPM)×100%. Specific lysis=% lysis with antibody—% lysis without antibody. Assays were performed in triplicate.

Superoxide Induction

U937 cells were used for measuring the ability of H22 to trigger a superoxide burst via FcγRI, (Pfefferkorn, L. C. and G. R. Yeaman (1994), Association of IgA-Fc receptors (FcxR) with Fce RIγ 2 subunits in U937 cells, *J. Immunol.* 153:3228; Hallet, H. B. and A. K. Campbell (1983). Two distinct mechanisms for stimulating of oxygen—radical production in polymorphonuclear leucocytes, *Biochem J.* 216:459). U937 cells were cultured for five days in RPMI-1640 (Gibco, Grand Island, N.Y.) with 10% FBS (Hyclone, Logan, Utah) in the presence of 100 U/ml IFN-γ (Genentech, S. San Francisco, Calif.) to induce differentiation and increased expression of FcγRI. On the day of the experiment, these differentiated cells were incubated for 20 minutes in fresh RPMI-1640 with 10% FBS at 37° C. The cells were then pelleted and resuspended at a concentration of 3×10$^6$ cells/ml in PBS supplemented with 1 mM CaCl$_2$, 1 mM MgCl$_2$, 11 mM glucose, and 100 μg/ml BSA (Sigma, St. Louis, Mo.). To trigger the release of superoxide, 100 μl of cells were added to 100 μl of a reaction solution containing 0. 1 mM luminol (Sigma, St. Louis, Mo.), 0.5 mM sodium vanadate (Sigma, St. Louis, Mo.), and either mab M22, H22, or 197 and placed in the luminometer at 22° C. Measurements of the spontaneous production of superoxide were made every 30 to 40 seconds starting immediately following the addition of the cells to the reaction solution in the luminometer. To compare the superoxide triggered by crosslinking FcγRI with M22, H22 or 197, each mAb was used at a concentration of 10 μg/ml. The production of superoxide in mV/sec was monitored for 20 minutes. MAb M22, M32.2 and 197 were added at various concentrations to establish the dose-responsiveness of superoxide production.

Results

Murine Ig V Region Genes

Ig V region cDNAs were prepared from M22 hybridoma RNA using primers specific for murine heavy and kappa constant regions and were amplified by PCR with the additional use of a series of primers based on sequences of known signal and/or 5' sequences of mature V regions. PCR products of the expected sizes for V$_H$ and V$_κ$ were obtained using the SH2BACK/CG1FOR and VK7BACK/CK2FOR primer combinations. Amplified DNA was digested with appropriate restriction enzymes, cloned into M13 and the sequence in both directions determined from at least 24 independent clones. The 4 N-terminal residues of V$_κ$ are encoded by the VKBACK primer.

The M22 V$_H$ and V$_κ$ are members of murine heavy chain subgroup IIID and kappa subgroup I, (Kabat, E. A. et al., (1991), *Sequences of Proteins of Immunological Interest,* 5th Ed., U.S. Department of Health and Human Services), respectively. Apart from the residue at L97, the amino acid sequence of the M22 V$_κ$ is identical to that from the murine anti-IgG mAb A17 (Shlomchik, M. et al., Variable region sequences of murine IgM anti-IgG monoclonal autoantibodies (rheumatoid factors). II Comparison of hybridonias derived bylipopolysaccharide stimulation and secondary protein immunization, *J. Exp. Med.* 165:970).

Humanized mAbs and Initial Characterization of their Binding

M22 V$_H$ FR showed greater homology (79%) to KOL (human subgroup III) than to NEWM (57%) (human subgroup II). To see how this difference might affect binding, heavy chains were constructed based either on NEWM V$_H$ including the murine residues Phe27, Ile28 and Arg71, or on KOL V$_H$ with no murine FR amino acids. Both humanized V$_H$ were partnered with the same REI-derived humanized light chain.

The affinity of the humanized mAbs was initially assessed by ELISA measuring the binding to FcγRI/IgM heavy chain fusion protein. The data showed that the KOL V$_H$/REI V$_κ$ mAb had the same binding as the chimeric mAb whereas the NEWM V$_H$/REI V$_κ$ mAb exhibited an approximate 5-fold lower affinity. The low binding of a nonspecific human IgG1 mAb showed that >95% of binding of the humanized mAbs was via the Fv portion rather than through the Fc domain.

While additional changes to the NEWM FR would be expected to restore binding affinity these could create novel epitopes which might provoke an unwanted immunological response. The KOL V$_H$/REI V$_κ$ mAb, designated H22, was therefore chosen for further examination of its binding characteristics.

Functional Characterization of mAbH22

A series of binding experiments were performed to establish the specificity and isotype of the H22 antibody. Peripheral blood leukocytes stained with fluorescein-conjugated M22 or H22 demonstrated specific binding to monocytes with approximately 10$^4$ binding sites per cell. In contrast, lymphocytes or unstimulated neutrophils had little or no specific binding (Table 1):

TABLE 1

Specific Binding of H22 to Monocytes

| Antibody | Monocytes | Lymphocytes | PMNs |
|---|---|---|---|
| M22 | 10,000[a] | <1000 | <1000 |
| H22 | 10,500 | <1000 | <1000 |

[a]Antibody sites per cell, average of duplicates

To demonstrate that the H22 binds to FcγRI at the same site as M22 and that it also binds as a ligand at the Fc binding domain, competition experiments with two anti-FcγRI murine mAb (M22 and M32.2) and a human IgG1 mAb were performed. Unconjugated H22 and M22 competed equivalently for either the binding of fluoresceinated M22 or fluoresceinated H22 in the presence of excess human IgG which saturated the Fc binding sites on FcγRI. As expected, the anti-FcγRI antibody M32.2 which binds to a different site on FcγRI than M22 (Guyre, P. M. et al., *J. Immunol.* 143:1650) was also unable to compete with the M22-FITC. In addition, the inhibition of H22-FITC by H22 and not by an irrelevant human IgG1 mAb confirmed the specificity of FcγRI binding via the V regions of H22.

H22, but not M22, was able to compete for Fc mediated binding to FcγRI by a fluorosceinated human IgG1. This experiment demonstrated that the Fc portion of H22 but not M22 bound to the Fc binding domain of FcγRI. This is consistent with the ability of the Fc portion of human IgG1 antibodies, but not murine IgG1, to bind FcγRI with high affinity.

Since the humanization of M22 was primarily to increase its immunotherapeutic potential, the binding activity of H22 to monocytes and cytokine-activated neutrophils was determined in the presence of human serum. H22-FITC bound with similar affinity to FcγRI on monocytes in the presence or absence of human serum. In contrast, the Fc-mediated binding of an irrelevant human IgG-FITC was completely inhibited by human serum. Likewise, H22-FITC bound with similar affinity to IFN-γ-treated neutrophils in the absence and in the presence of human serum. Collectively, the data demonstrated that H22 binds both via its V regions to a site distinct from the Fc binding domain and via its Fc region to the ligand binding domain of FcγRI. The former binding activity effectively overcomes antibody blockade of human IgG 1.

Functional Activity of H22 BsAb

The foremost application of anti-FcγRI antibodies for immunotherapy is the development of BsAbs which link FcγRI-bearing effector cells to a tumor cell, a virus, or a virally-infected cell. Such BsAb have been developed with M22; therefore, a comparison was made of the ability of the M22 anti-tumor BsAb (520C9×M22) and a corresponding H22 BsAb (520C9×H22) to mediate cytotoxicity. These BsAbs consisted of H22 or M22 Fab' chemically conjugated to the Fab' of an anti-HER2/neu antibody (520C9), and thus were specific for the effector cell trigger molecule FcγRI and the tumor antigen.

Comparison of M22-derived and H22-derived BsAbs was done by ADCC assays. M22- and H22-derived BsAbs mediated the killing of HER2/neu overexpressing SKBR-3 cells. Both the murine and humanized BsAbs exhibited similar levels of lysis of antigen bearing target cells. In addition, both BsAb retained ADCC activity in the presence of human serum, while excess M22 F(ab')$_2$ resulted in complete inhibition of killing. Taken together these results show that the H22 BsAb-induced lysis is mediated through the M22 epitope and that the ADCC is FcγRI specific.

Finally, the ability of H22 and M22 to stimulate superoxide production by the monocyte-like cell line U937 was evaluated. M22, which binds to the FcγRI only by its V regions, induced a very low level oxygen burst, presumably because it is unable to cross-link the receptor efficiently. However, H22, which can cross-link FcγRI by binding as a ligand via its Fc domain and, additionally, as an antibody via its Fv, induced a more substantial release of superoxide.

Example 2

Generation of Functional H22-Epidermal Growth Factor Fusion Protein

Materials and Methods

Expression Vectors and Cloning

Expression vectors for the genomic clones of the heavy (pSVgpt) and light (pSVhyg) chains of H22 are as described in International Patent Application Publication Number: WO 94/10332 entitled, *Humanized Antibodies to Fc Receptors for Immunoglobulin G on Human Mononuclear Phagocytes*. For the Fab-ligand fusion construct, it was unnecessary to alter the light chain. For the heavy chain, however, the CH2 and CH3 domains had to be removed and replaced with the coding sequences of the ligands. The heavy chain vector contains two BamHI sites, one in the intron between VH and CH1, and the other just downstream of CH3. Using the BamHI restriction sites, DNA encoding the constant domains were replaced by a truncated version encoding only CH1 and most of the hinge. To do this, the polymerase chain reaction (PCR) was utilized to engineer the new C-terminus of the heavy chain fragment with the alterations shown in FIG. 1.

The construct shown in FIG. 1 [C], consisting of a translation termination codon downstream of the cloning restriction sites, XhoI and NotI, and upstream of a BamHI site which was used to clone the new PCR generated CHI fragment downstream of VH, was used to generate the fusion protein constructs. The cloning sites, which are located downstream of most of the hinge in order to retain flexibility between the Fd and ligand domains, was used to insert DNA encoding EGF or other ligands. Also, the single Cys residue has been retained from the previous construct to allow conjugation for the formation of dimeric molecules.

DNA encoding the ligands were amplified by PCR to have a XhoI site on the N-terminus and a NotI site on the C-terminus of the coding region, and then inserted in the proper reading frame into the same sites of the newly engineered H22 heavy chain truncated fragment described above. cDNA encoding epidermal growth factor (EGF) was obtained from the ATCC (#59957). Only DNA encoding the 53 amino acid residues of mature EGF out of the approximately 1200 residue precursor was cloned beginning with Asn 971 and ending with Arg 1023 (Bell, G. I., Fong, N. M., Stempien, M. M., Wormsted, M.A., Caput, D., Ku. L., Urdea, M. S., Rall, L. B. & Sanchez-Pescador, R. Human Epidermal Growth Factor Precurser: cDNA Sequence, Expression In Vitro and Gene Organization. Nucl. Acids Res. 14: 8427–8446,1986.).

Expression

The murine myeloma NSO (ECACC 85110503) is a non-Ig synthesizing line and was used for expression of the fusion proteins. The final expression vector, a pSVgpt construct with DNA encoding H22 Fd fused in frame to EGF was transfected by electroporation using a BioRad Gene Pulser to NS0 which had been previously transfected with the pSVhyg construct containing DNA encoding H22 light chain. These polypeptides were expressed by an Ig promoter and Ig enhancer present in the vectors, and secreted by the mAb 22 heavy chain signal peptide located on the N-terminus of the constructs. One or two days after transfection, mycophenolic acid and xanthine were added to the media to select for cells that took up the DNA. Individual growing colonies were isolated and subcloned after binding activity was demonstrated by ELISA.

Purification

Figure 2:
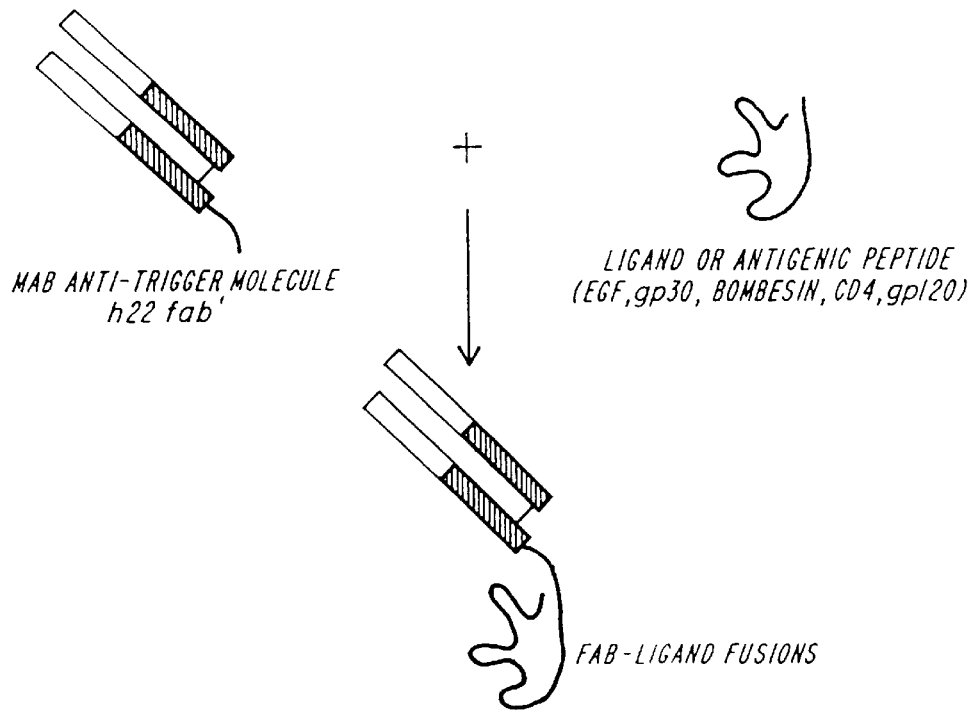
FIG. 2 is a schematic representation of the generation of anti-Fc receptor-ligand bispecific molecules.

Cells expressing the H22-EGF fusion protein were subcloned and expanded. The fusion protein-expressing clone was expanded and grown in spinner cultures and the supernatant was clarified and concentrated. Small scale purification was performed by affinity chromatography on an anti-human kappa chain affinity column (Sterogene. Carlsbad, Calif.). The purified protein was analyzed by SDS-PAGE on a 5–15% acrylamide gradient gel under nonreducing conditions. FIG. 2 is a schematic representation of the generation of anti-Fc receptor-ligand fusion proteins.

Bispecific Flow Cytometry

Figure 3:
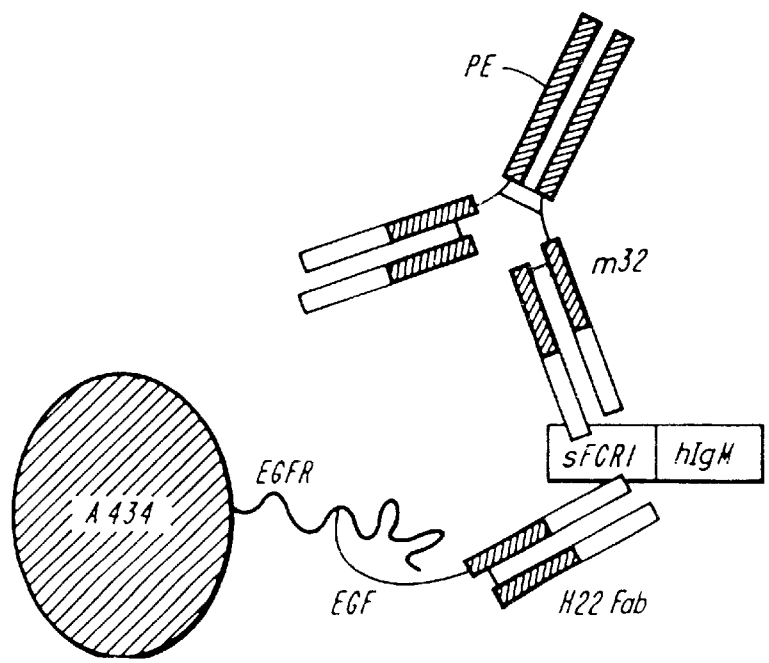
FIG. 3 is a schematic representation of the flow cytometric assay used for testing the activity of the humanized Fc γ receptor- epidermal growth factor fusion protein.

To show that the fusion protein is capable of binding both FcγRI and EGFR simultaneously, a flow cytometric assay has been developed (FIG. 3). In this assay different concentrations of H22-EGF fusion protein or the bispecific antibody, BsAb H447 (H22×H425, a humanized version of the murine monoclonal antibody M425, which binds EGFR at the ligand binding site (E. Merck) was incubated with 1483 cells, a cell line which expresses the EGF receptor (EGFR) (ATCC, Rockville, Md.). After washing, a supernatant containing a fusion protein consisting of the extracellular domain of FcγRI and the Fc portion of human IgM was added. Finally, a Phycoerythrin (PE)-labeled mAb (32.2), that binds Fcγ RI at a site that is distinct from that bound by mAb 22, was added. The cells were then analyzed by FACSCAN. Alternatively, binding to EGFR was blocked by excess (100 μg/ml) whole murine mAb 425 (E. Merck), and binding of BsAb or fusion protein was detected by PE-labeled anti-human IgG.

ADCC

ADCC mediated by the fusion protein was determined using a $^{51}$Cr killing assay. The EGFR overexpressing cell line, A431, was used as targets for lysis by human monocytes cultured in γ-interferon (IFN-γ) for 24 hours. Targets were labeled with 100 μi of $^{51}$Cr for 1 hour prior to combining with effector cells and antibodies in a U-bottom microtiter plate. After incubation for 5 hours at 37° C. supernatants were collected and analyzed for radioactivity. Cytotoxicity was calculated by the formula: % lysis=(experimental CPM—target leak CPM/detergent lysis CPM—target leak CPM)×100%. Specific lysis =% lysis with antibody—% lysis without antibody. The ability of the fusion protein to mediate ADCC was compared with that of the respective BsAb. The assay was also performed in the presence of 25% human serum to demonstrate that IgG or other factors found in human serum will not inhibit fusion protein-mediated ADCC.

F. Other Fusion Proteins

Other fusion proteins, such as H22- gp30 (heregulin) (Dr. Ruth Lupu, Georgetown University), CD4 (AIDS Repository), gp120 (AIDS Repository), and bombesin. The bombesin fusion, however, was generated in a somewhat different manner from the others because it is only a short peptide (14 amino acid residues). Instead of amplifying cDNA encoding bombesin using PCR, DNA oligomers encoding the sense and anti-sense strands of bombesin were hybridized to create the gene. The oligomers had overlapping ends that did not hybridize but instead created sticky ends for a XhoI site on the N-terminus and a NotI site on the C-terminus so that it could be cloned into the H22 heavy chain expression vector.

Results

Purification

NS0 cells expressing the H22 kappa chain were transfected with the H22-EGF heavy chain construct and clones selected for resistance to mycophenolic acid and xanthine were expanded and the fusion protein was affinity-purified from the supernatant on an anti-human kappa column (Sterogene, Carlsbad, Calif.). The purified protein was analysed by SDS-PAGE. The purified protein migrated at an apparent molecular weight of 50–55 kDa, indicating that the fusion protein is expressed as a monomer, not a disulfide-linked dimer. In addition, a band was seen at an apparent molecular weight of 25 kDa and is probably free light chain.

Binding specificity

Figure 4:
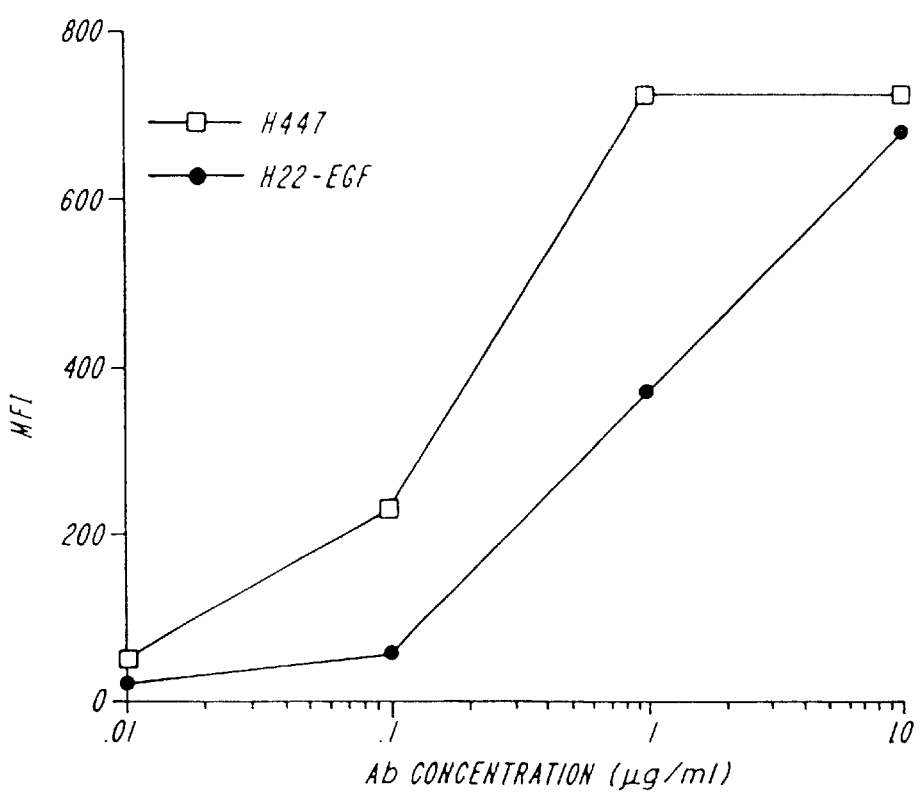
FIG. 4 is a graph, which plots Mean Fluorescence Intensity (MFI) an indication of the binding of various concentrations of epidermal growth factor (EGF) fusion protein (H22-EGF fusion) and the fully humanized bispecific (BsAb) H447 to EGF receptor (EGFR) expressing 1483 cells.

To demonstrate that the fusion protein could bind FcγRI and EGFR simultaneously a bispecific FACS assay was devised. FIG. 4 shows that both the chemically-linked, fully-humanized BsAb H447 (H22 (anti-FcγRI)×H425), which was made as described in the following Example 3, and the H22-EGF fusion protein bound to EGFR expressing cells (1483) and soluble FcγRI simultaneously in a dose-dependent fashion.

Figure 5:
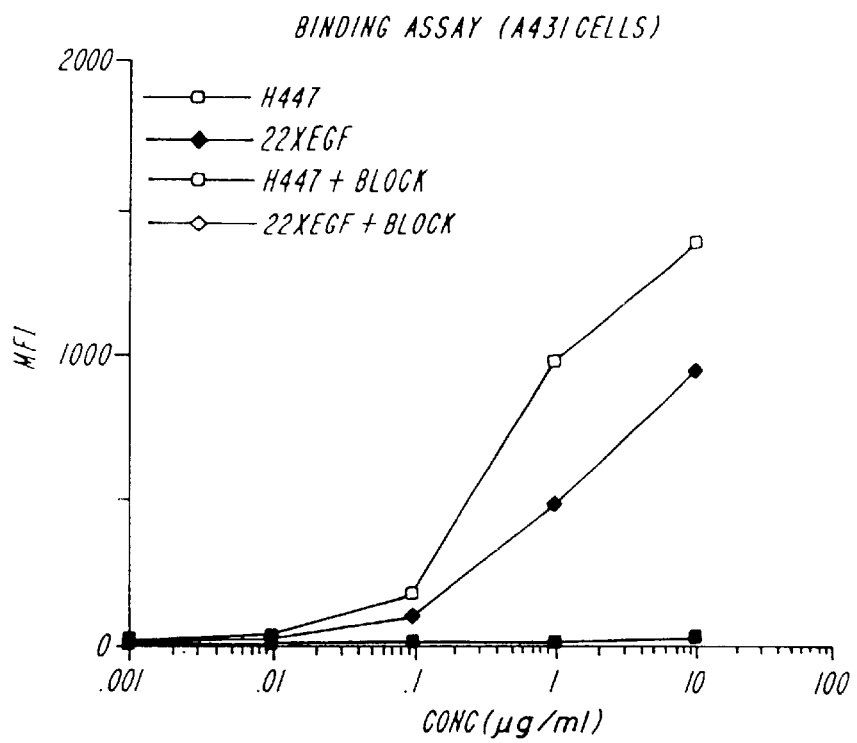
FIG. 5 is a graph, which plots the binding of various concentrations of the EGF fusion protein or the BsAb H447 to A431 cells in the presence and absence of murine antibody M425, which binds EGFR.

The EGFR-specificity of the fusion protein was demonstrated by the ability of the murine mAb, M425, which binds EGFR at the ligand binding site, to inhibit fusion protein or H22×H425 binding. Various concentrations of either the BsAb H447, or of the H22-EGF fusion protein were incubated with A431 cells in either the presence or absence of an excess of M425. FIG. 5 shows that binding of both the BsAb and the fusion protein were inhibited by M425, demonstrating the specificity of the fusion protein for EGFR.

ADCC

Figure 6:
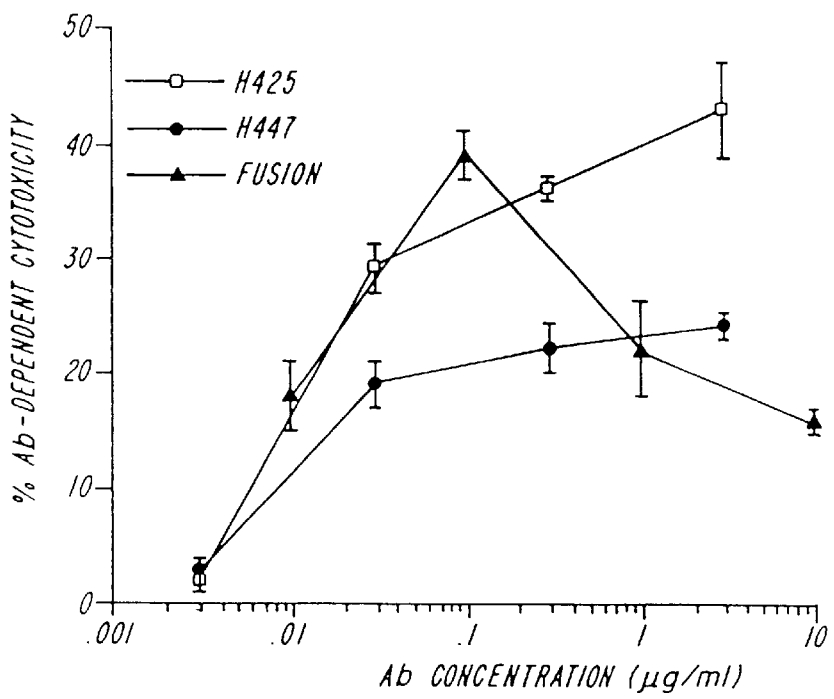
FIG. 6 is a graph, which plots the antibody dependent cytotoxicity (ADCC) resulting from the binding of various concentrations of the EGF fusion protein, BsAb H447 or the H425 antibody to A431 cells.
Figure 7:
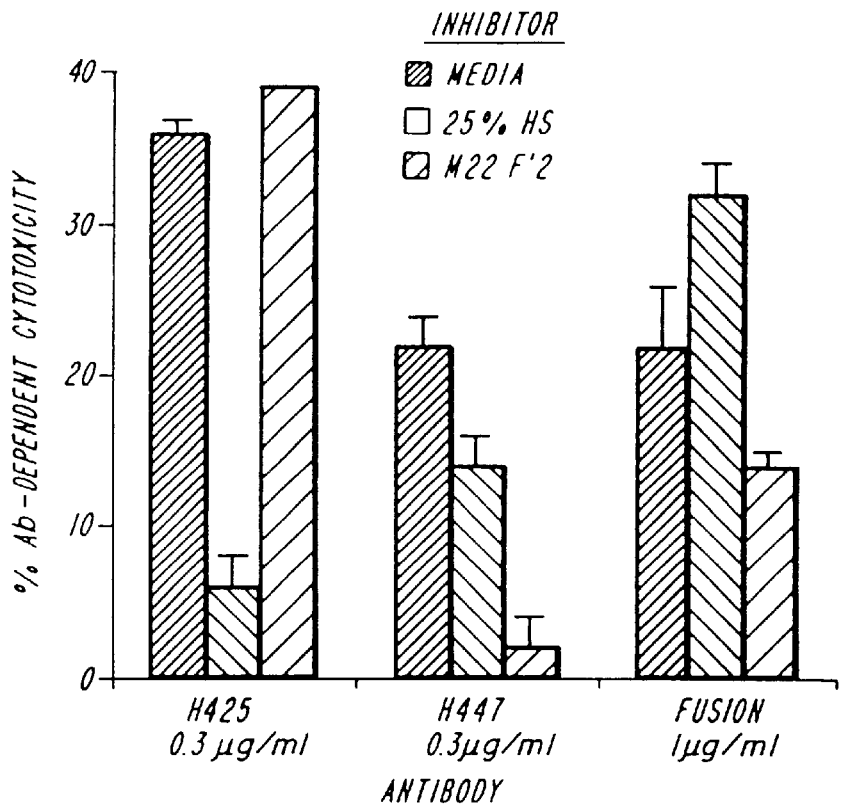
FIG. 7 is a bar graph which plots the ADCC resulting from the binding of EGF fusion protein, BsAb H447 or the H425 antibody in the presence of media alone, media containing 25% human serum (HS) or media containing a Fab fragment of the Fcγ receptor antibody m22.

The ability of the fusion protein to mediate ADCC was analyzed using A431 cells as targets. Human monocytes cultured for 24 hours in the presence of IFN-γ were used as effector cells. FIG. 6 demonstrates the whole antibody, H425, the BsAb H447 (H22×H425) and the fusion protein mediated dose-dependent lysis of A431 cells. FIG. 7 demonstrates that while ADCC mediated by the whole antibody is inhibited by 25% human serum (25% HS), ADCC mediated by the fusion protein was not inhibited by human serum and, in this particular experiment, fusion protein-mediated ADCC was enhanced by human serum. These results support the clinical utility of these molecules by demonstrating that the fusion protein was capable of killing EGFR-overexpressing cells, even in the presence of Fcγ RI-expressing effector cells as would be present in vivo.

Example 3

Production of Bispecific Antibodies from Modified Humanized Antibody Fragments

Materials and Methods

Expression Vectors and Cloning

Expression vectors for the genomic clones of the heavy (pSVgpt) and light (pSVhyg) chains of H22 were as described in International Patent Application Publication Number: WO 94/10332 entitled, Humanized Antibodies to Fc Receptors for Immunoglobulin G on Human Mononuclear Phagocytes. For the Fab' construct, it was unnecessary to alter the light chain. For the heavy chain, however, the CH2 and CH3 domains had to be removed and replaced with a termination codon. The heavy chain vector contains two BamHI sites, one in the intron between VH and CH1, and the other just downstream of CH3. Using the BamHI restriction sites, DNA encoding the constant domains were replaced by a truncated version encoding only CH1 and most of the hinge. To do this, The polymerase chain reaction (PCR) was utilized to engineer the new C-terminus of the heavy chain fragment with the alterations shown in FIG. 1. FIG. 1 [B] shows the alterations for generation of a truncated single-sulfhydryl version.

Expression

The murine myeloma NSO (ECACC 85110503) is a non-Ig synthesizing line and was used for expression of the modified H22 antibody. The final expression vector, a pSVgpt construct with DNA encoding H22 Fd was cotransfected with the pSVhyg construct containing DNA encoding H22 light chain by electroporation using a BioRad Gene Pulser. These polypeptides were expressed by an Ig promoter and Ig enhancer present in the vectors, and secreted by the mAb 22 heavy chain signal peptide located on the N-terminus of the constructs. One or two days after transfection, mycophenolic acid and xanthine were added to the media to select for cells that took up the DNA. Individual growing colonies were isolated and subcloned after FcγRI binding activity was demonstrated.

Purification

The single sulfhydryl form of the H22 antibody and the whole H425 (anti-EGFR) antibody were produced by in vitro cultivation of the respective transfected NSO cells. The H425 was purified by protein A affinity chromatography. The single sulfydryl form of the antibody H22 was purified by ion exchange chromatography using Q-Sepharose followed by SP-Sepharose (Pharmacia, Piscataway, N.J.). The purity of the single sulfhydryl form of the H22 antibody was assessed by SDS-PAGE.

Generation of Bispecific Antibody (BsAb)

BsAb was constructed using the method of Glennie et al. (Glennie, M. J. et al., (1987), Preparation and performance of bispecific F(ab' gamma)$^2$, antibody containing thioether-linked Fab' gamma fragments, *J. Immunol.*, 139:2367). The F(ab')$_2$ of H425 was generated by limited pepsin proteolysis in 0.1M citrate buffer, pH 3.5 and the F(ab')$_2$ purified by ion exchange chromatography. The mAbs were reduced by addition of 20 mM mercaptoethanolamine (MEA) for 30 minutes at 30° C. The Fab' fragments were applied to a Sephadex G-25 column equilibrated in 50 mM sodium acetate, 0.5 mM EDTA, pH 5.3 (4° C.). Ortho-phenylenedimaleimide (o-PDM, 12 mM) dissolved in dimethyl formamide and chilled in a methanol/ice bath was added (one half volume) to the H22 Fab' and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the H22 Fab'-maleimide was added to the H425 Fab' at a 1.2:1 molar ratio. The reactants were concentrated under nitrogen to the starting volume using a Diaflo membrane in an Amicon chamber (all at 4° C.). After 18 hours the pH was adjusted to 8.0 with 1M Tris-HCl, pH 8.0. The mixture was then reduced with 10 mM MEA (30 minutes, 30° C.) and alkylated with 25 mM iodoacetamide. The bispecific F(ab')$_2$ was separated from unreacted Fab's and other products by a Superdex 200 (Pharmacia, Piscataway, N.J.) column equilibrated in PBS.

Bispecific Flow Cytometry

Figure 8:
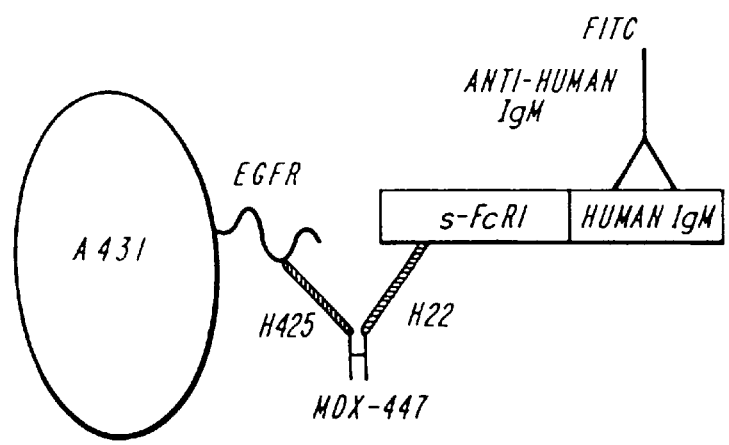
FIG. 8 is a schematic representation of the flow cytometric assay used for testing the activity of BsAb 447 generated either by the o-PDM or the DTNB method.

To show that BsAb generated by the o-PDM method as well as that generated by the DTNB method are capable of binding both FcγRI and EGFR simultaneously, a flow cytometric assay has been developed (FIG. 8). In this assay different concentrations of the two BsAbs were incubated with A431 cells, a cell line which expresses the EGF receptor (EGFR). After washing, a supernatant containing a fusion protein consisting of the extracellular domain of FcγRI and the Fc portion of human IgM was incubated with the cells. Finally, the cells were incubated with a FITC-labeled anti-human IgM-specific antibody. The cells were then analyzed by FACSCAN.

ADCC

BsAb-mediated ADCC was determined using a $^{51}$Cr killing assay. The EGFR overexpressing cell line, A431, was used as targets for lysis by human monocytes cultured in γ-interferon for 24 hours. Targets were labeled with 100 μCi of $^{51}$Cr for 1 hour prior to combining with effector cells and antibody in a flat-bottomed microtier plate. After incubation for 16 hours at 37° C. supernatants were collected and analyzed for radioactivity. Cytotoxicity was calculated by the formula: % lysis=(experimental CPM—target leak CPM/detergent lysis CPM—target leak CPM)×100%. Ab-dependent lysis=% lysis with antibody—% lysis without antibody.

Results

Purification

NSO cells were cotransfected with the truncated H22 heavy chain construct and the intact kappa chain construct. Clones selected for resistance to mycophenolic acid and xanthine were expanded and the protein was purified from the supernatant by Q-Sepharose followed by SP-Sepharose ion exchange chromatography. The purified protein was analyzed by SDS-PAGE. The purified protein migrated at an apparent molecular weight of 50 kDa, indicating that the protein is expressed as a monomer, not a disulfide-linked dimer.

Construction and Characterization of a BsAb Composed of single Sulfhydryl H22 Linked to Fab' of H425 (Anti-EGFR)

Figure 9:
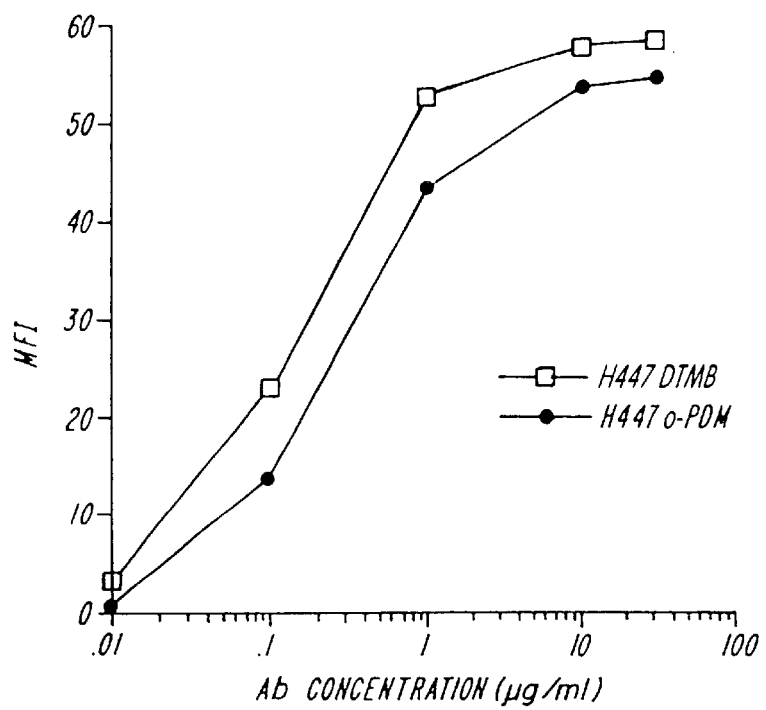
FIG. 9 is a graph, which plots the MFI of various concentrations of o-PDM and DTNB derived BsAb 447 to EGFR and expressing A431 cells FcγRI.

A BsAb was constructed where the single sulfhydryl form of H22 was linked to the Fab' fragment of H425, a humanized anti-EGFR mAb. The BsAb was generated using o-PDM as a linker by the method of Glennie et al. (Glennie, M. J. et al., (1987), Preparation and performance of bispecific F(ab' gamma)$^2$, antibody containing thioether-linked Fab' gamma fragments, *J. Immunol.*, 139:2367). The activity of this BsAb was compared to one generated by the DTNB method using Fab' fragments made from pepsin digestion and reduction of whole H22. To demonstrate that these BsAbs could bind FcγRI and EGFR simultaneously a bispecific FACS assay was devised. FIG. 9 shows that both the o-PDM-linked BsAb and the BsAb made by the DTNB method bound EGFR on A431 cells and soluble FcγRI simultaneously in a dose-dependent fashion.

Figure 10:
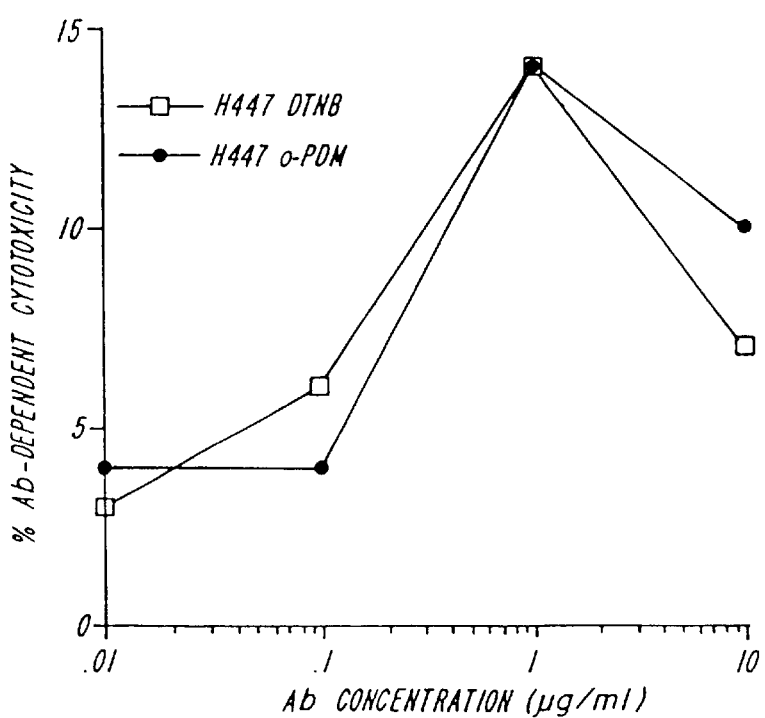
FIG. 10 is a graph, which plots the antibody dependent cytotoxicity resulting from the binding of o-PDM and DTNB derived BsAb 447 to A431 cells.

The ability of the two BsAbs to mediate ADCC was analyzed using A431 cells as targets. Human monocytes cultured for 24 hours in the presence of IFN-γ were used as effector cells. FIG. 10 demonstrates the two BsAbs mediated dose-dependent lysis of A431 cells in a comparable fashion. These results demonstrated that BsAb generated from the truncated, single sulfhydryl form of H22 was capable of killing EGFR-overexpressing cells in the presence of FcγRI-expressing effector cells.

Example 4

Production of Trivalent Antibodies

Materials and Methods

Cell Lines and Antibodies, M22, 520C9, H425, SKBR3 and A431

M22 and 520C9 were purified from hybridoma supernatant by ion exchange chromatography (Pharmacia, Piscataway, N.J.) and 520C9 was further purified by protein A affinity chromatography (Pharmacia, Piscataway, N.J.). H425 was purified from hybridoma supernatant by protein A affinity chromatography (Pharmacia, Piscataway, N.J.). The M22-and 520C9- producing murine hybridoma were described previously (Guyre et al., (1989) Monoclonal antibodies that bind to distinct epitopes on FcgRI are able to trigger receptor function, *J. Immunol.* 1435, 1650–1655; Frankel et al., (1985) Tissue distribution of breast cancer-associated antigens defined by monoclonal antibodies, *J. Biol. Response Modifiers*, 4:273–286). The murine myeloma NSO (ECACC 85110503) is a non-Ig synthesizing line and was used for the expression of the humanized mAb, H425 (Kettleborough et al., (1991) Humanization of a mouse monoclonal antibody by CDR-grafting: the importance of framework residues on loop conformation, *Protein Eng.*, 4:773). SKBR-3, (ATCC, 10801 University Blvd. Manassas Va. 20110-2209 human breast carcinoma cell line that overexpresses the HER2/neu protooncogene, and A431 (ATCC, Manassas Va.), a human squamous carcinoma cell line that overexpresses EGFR (ATCC, Manassas Va.) were cultivated in Iscove's Modified Dulbecco's Medium (IMDM, Gibco, Grand Island, N.Y.).

Neutrophil Preparation

Neutrophils are separated from mononuclear cells by ficoll hypaque (Pharmacia, Piscataway, N.J.) gradient separation. To up-regulate $F_{c\gamma}RI$, neutrophils are treated with cytokines. Neutrophils are cultured for 24–48hrs (37° C., 5% $CO_2$) in AIM V media (Gibco, Grand Island, N.Y.) containing 2.5% normal human serum type AB (Sigma, St. Louis, Mo.), 50 ng/ml G-CSF (Kindly provided br R. Repp, U. of Erlanger, Germany) and 100 IRU/ml IFN-γ.

Conjugation Method

BsAb were constructed using the method of Glennie et al (Glennie, M. J. et al., (1987), Preparation and performance of bispecific F(ab' gamma)$^2$, antibody containing thioether-linked Fab' gamma fragments, *J. Immunol.*, 139:2367). mAbs M22, 520C9 (anti-HER2/neu, 33), and H425 (anti-EGFR) antibodies were produced by in vitro cultivation of the respective hybridoma cells. The F(ab')$_2$ of each antibody were generated by limited pepsin proteolysis in 0.1M citrate buffer, pH 3.5 and the F(ab')$_2$ purified by ion exchange chromatography mAbs M22 and H425 were reduced to Fab' by addition of 10 mM mercaptoethanolamine (MEA) for 30 minutes at 30° C. The Fab' fragments were applied to a Sephadex G-25 column equilibrated in 50 mM Na Acetate, 0.5 mM EDTA, pH 5.3 (4° C.). Ortho-phenylenedimaleimide (o-PDM,12 mM) dissolved in dimethyl formamide and chilled in a methanol/ice bath was added (one half volume) to the murine 22 Fab' and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the M22 Fab'-maleimide was added to the H425 Fab' at a 1:1 molar ratio. The reactants were concentrated under nitrogen to the starting volume using a Diaflo membrane in an Amicon chamber (all at 4° C.). After 18 hours the pH was adjusted to 8.0 with 1M Tris-HCl, pH 8.0. The mixture was then reduced with 10 mM MEA (30 minutes, 30° C.) and alkylated with 25 mM iodoacetamide. The bispecific F(ab')$_2$ as separated from unreacted Fab's and other products by a Superdex 200 (Pharmacia, Piscataway, N.J.) column equilibrated in phosphate buffered saline (PBS). The BsAb M22×520C9 was made in a similar fashion except that 520C9 was used instead of H425.

Figure 11A:
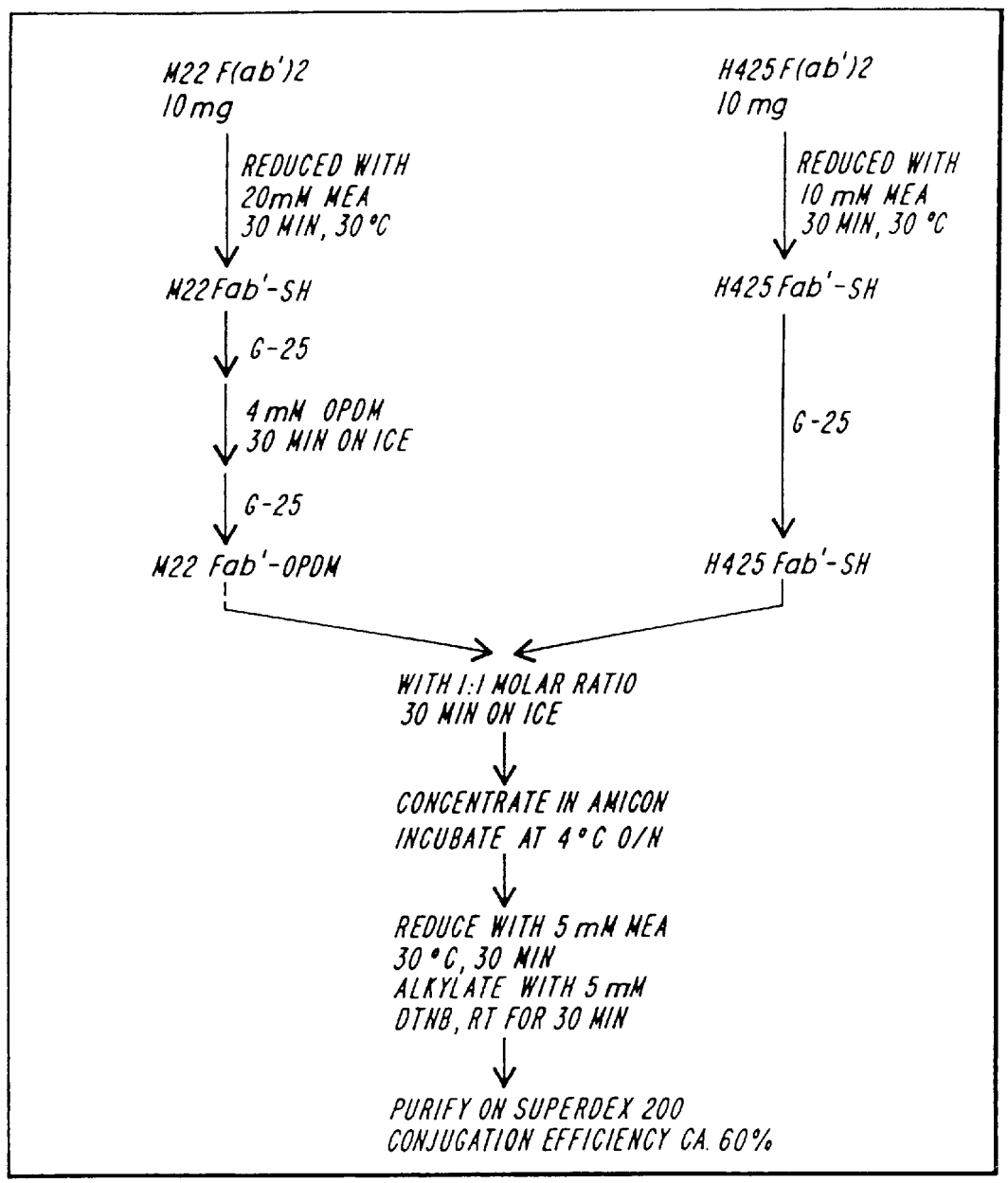
FIG. 11 is a flow chart that depicts the construction of trispecific antibodies.
Figure 11B:
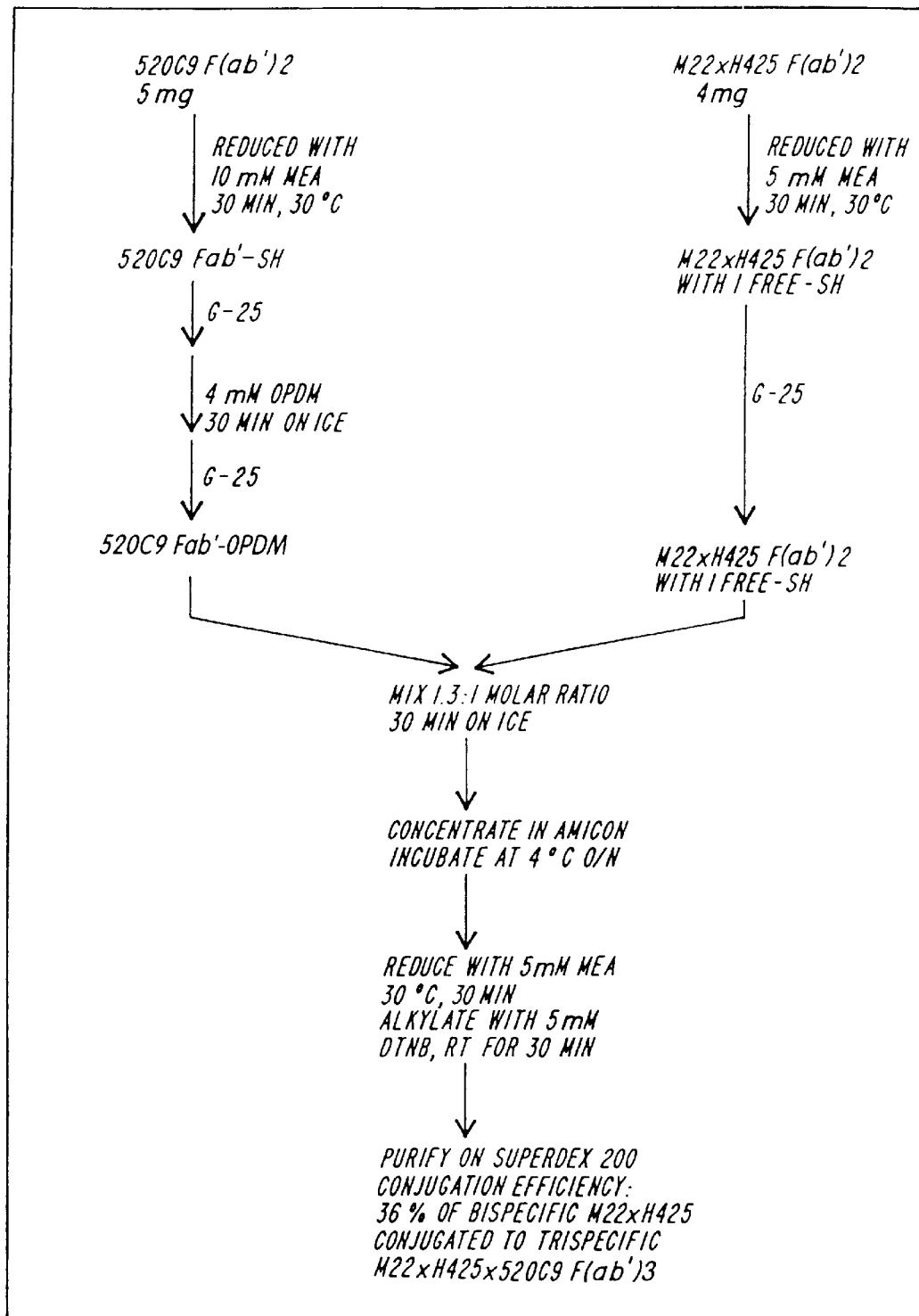

Trispecific antibody composed of M22×H425×520C9 was made in two stages (FIG. 11). In the first stage, M22 was linked to H425 as described above to create the M22×H425 BsAb except that rather than a final reduction and alkylation, the reactants were treated with DTNB to block the remaining free sulfhydryl groups. The bivalent BsAb was purified by gel filtration on a Superdex 200 column, reduced to F(ab')$_2$(SH) and mixed in a 1:1 molar ratio with o-PDM-treated 520C9. The resulting trispecific F(ab')3 was purified on a Superdex 200 column. The TsAb was analyzed by HPLC size exclusion chromatography using a TSK 3000 column (Togo Haas, Japan). Using the same procedure as above another TsAb comprising m22 Fab'×32.2 Fab'×m22 Fab' has been constructed.

Bispecific Flow Cytometry

The TsAb can bind to EGFR and $F_{c\gamma}RI$ simultaneously or to HER2/neu and $F_{c\gamma}RI$ simultaneously. Either A431 cells (high EGFR-expressing cells) or SKBR-3 cells (high HER2/neu-expressing cells) were incubated with various concentrations of BsAbs (M22×520C9 or M22×H425) or with the TsAb, M22×H425×520C9. The cells were washed and then incubated with the soluble $F_{c\gamma}RI$. Soluble $F_{c\gamma}RI$ binding was detected with mAb 32.2-FITC which binds $F_{c\gamma}RI$ at a site that is distinct from the 22 binding site. The cells were then analyzed by FACSCAN.

ADCC

Either SKBR-3 cells or A431 cells were used as targets for lysis by cytokine activated neutrophils. Targets were labeled with 100 μCi of $^{51}Cr$ for 1 hour prior to combining with neutrophils and antibodies in a U-bottom microtiter plate. After incubation for 16 hours at 37° C. supernatants were collected and analyzed for radioactivity. Cytotoxicity was calculated by the formula: % lysis=(experimental CPM—target leak CPM/detergent lysis CPM—target leak CPM)× 100%. Specific lysis=% lysis with antibody—% lysis without antibody. Assays were performed in triplicate.

FcγRI Modulation Assay

Figure 18A:
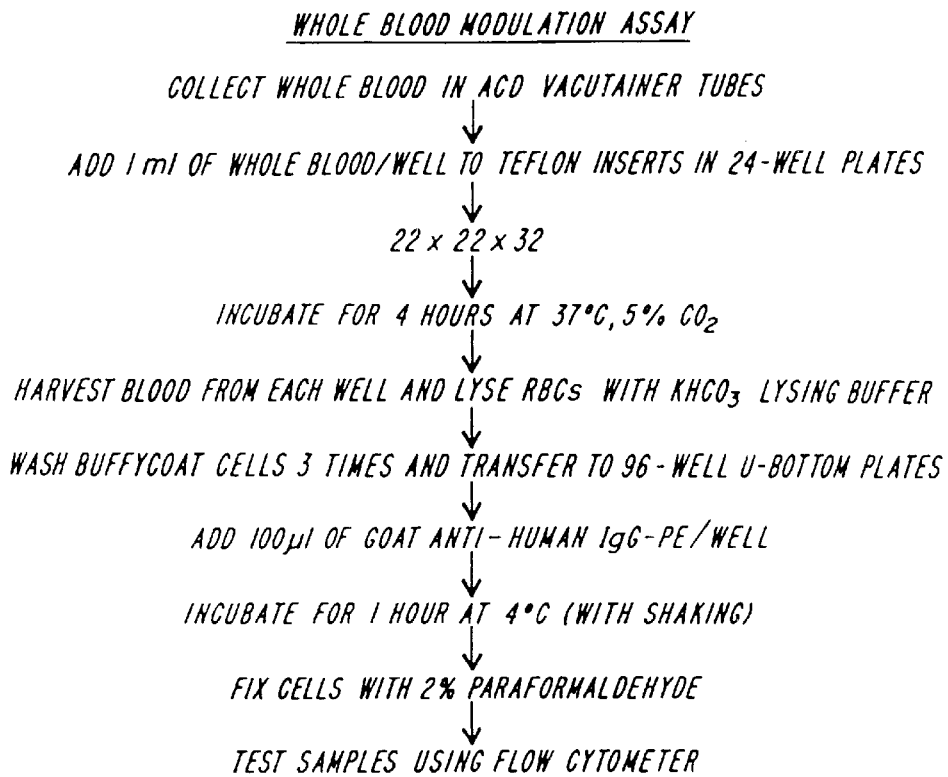
FIG. 18 is a flow chart for a whole blood modulation assay (panel A) and the results from the assay (panel B). This trivalent antibody rapidly modulates $F_{c\gamma}RI$ from the surface of monocytes.
Figure 18B:
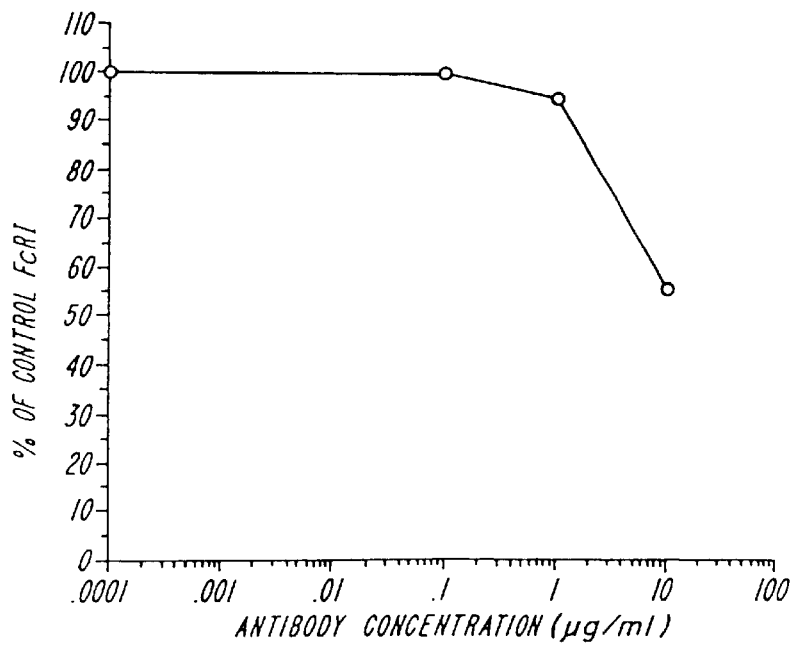

The M22×32.2×M22 BsAb was used for modulation of FcγRI on monocytes in whole blood. The assay procedure is shown in the enclosed flow chart (see FIG. 18A). FIG. 18B shows that treatment with 10 μg/mL of this BsAb decreased the FcγRI expression on monocytes to approximately 50% of the level prior to BsAb treatment.

Results

Construction and Biochemical Characterization of the TsAb

Figure 12:
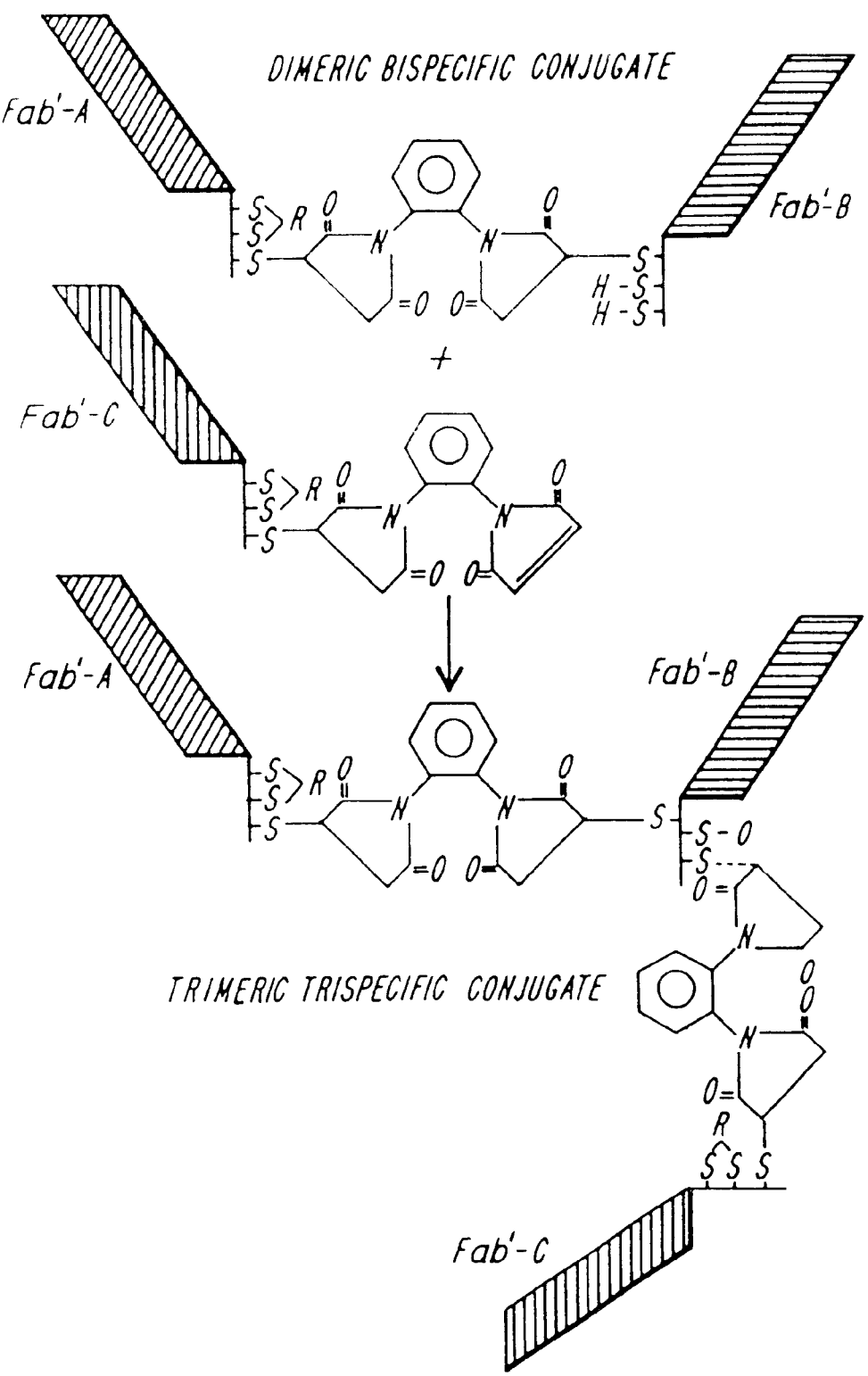
FIG. 12 depicts the transformation of a bivalent, bispecific antibody into a trivalent, trispecific antibody (TsAb). The bivalent, bispecific conjugate is reduced and mixed with o-PDM-treated 520C9 Fab' resulting in the TsAb.

TsAb was made according to the flow chart depicted in FIG. 11. In the first stage of the procedure, M22 was coupled to H425, treated with DTNB, and the resulting bispecific F(ab')$_2$ purified by gel filtration. In the second stage, this bispecific F(ab')$_2$ was reduced and mixed with o-PDM-treated 520C9 Fab' resulting in the TsAb, M22×H425× 520C9. This TsAb is depicted schematically in FIG. 12. In this figure, Fab'-A represents M22, Fab'-B represents H425, and Fab'-C represents 520C9.

Binding (Bs FACS)

Figure 13A:
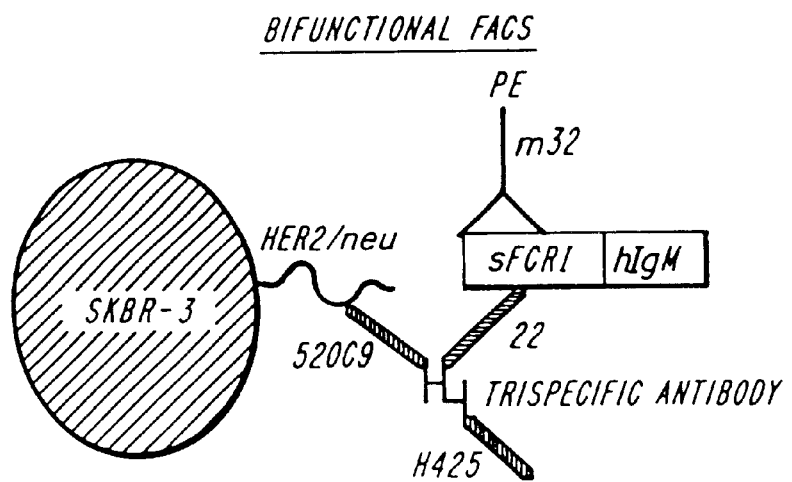
FIG. 13 depicts a bifunctional fluorescence-activated cell sorting assay for HER2/neu (panel A) and EGFR (panel B).
Figure 13B:
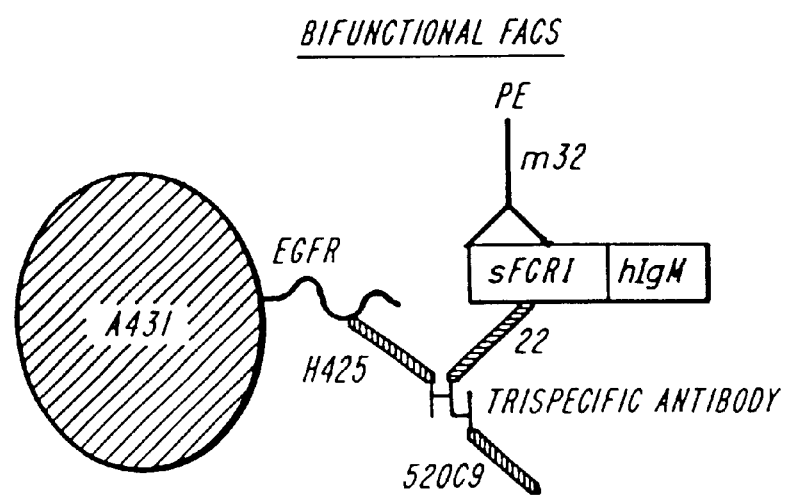
Figure 14:
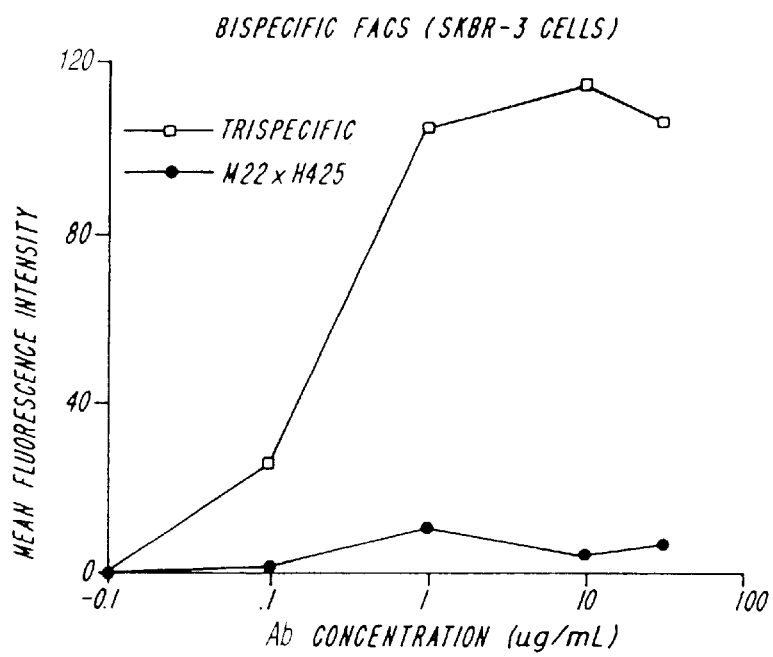
FIG. 14 is a graph which plots the binding of various concentrations of antibody, either BsAb or TsAb, to target cells. Mean Fluorescence Intensity (MFI) increases as Ab concentration increases. It shows that the TsAb bound both HER2/neu on SKBr-3 cells and soluble FcγRI simultaneously in a dose-dependent fashion.
Figure 15:
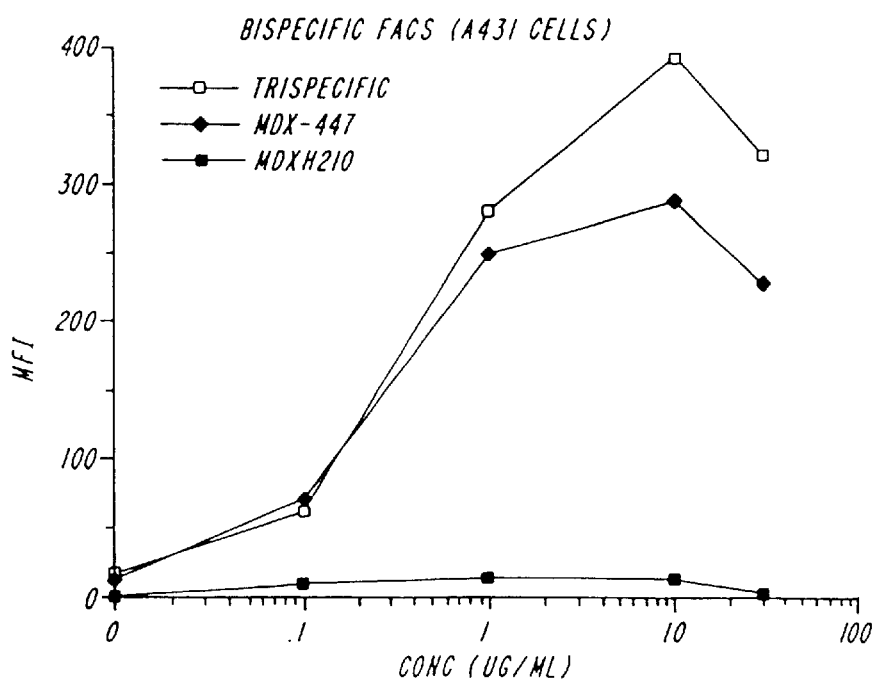
FIG. 15 is a graph that shows the TsAb bound both EGFR on A431 cells and soluble FcγRI simultaneously in a dose-dependent fashion. The assay is similar to that used in FIG. 14.

To demonstrate that the TsAb, M22×H425×520C9, could bind $F_{c\gamma}RI$ and HER2/neu simultaneously a bispecific FACS assay was devised. This assay is depicted schematically in FIG. 13A. FIG. 14 shows that both the TsAb bound HER2/neu on SKBR-3 cells and soluble $F_{c\gamma}RI$ simultaneously in a dose-dependent fashion. The BsAb, M22×H425, generated negligible signal in this assay over a wide range of concentrations. To demonstrate that the TsAb, M22×H425×520C9, could bind $F_{c\gamma}RI$ and EGFR simultaneously a similar assay was devised using the EGFR-overexpressing cell line, A431, in the case. This assay is depicted schematically in FIG. 13B. FIG. 15 shows that both the TsAb and the BsAb, M22× H425, bound EGFR on A431 cells and soluble $F_{c\gamma}RI$ simultaneously in a dose-dependent fashion. The BsAb, M22× 520C9, generated negligible signal in this assay over a wide range of concentrations.

ADCC

Figure 16:
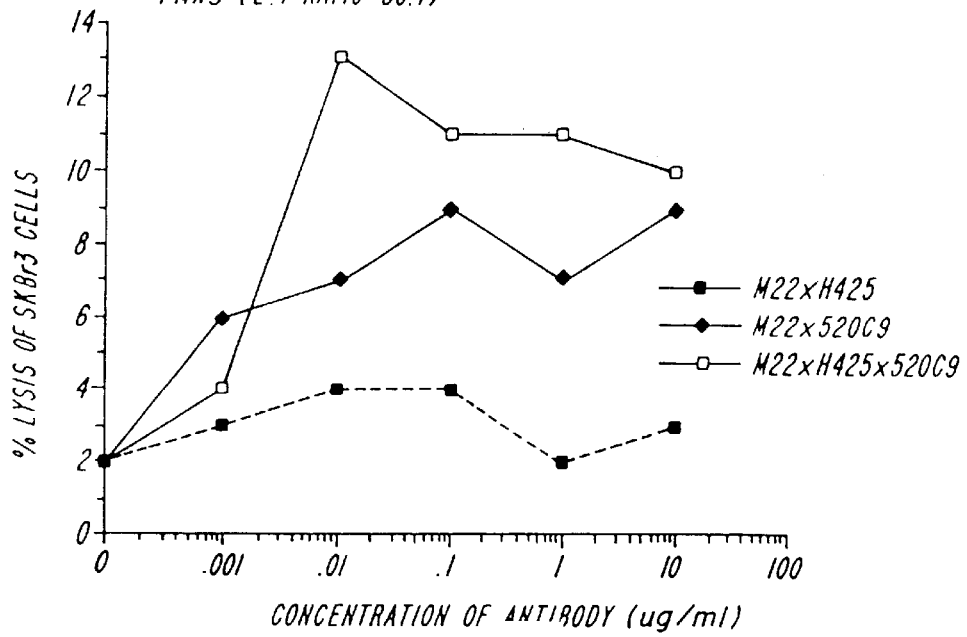
FIG. 16 is a graph that shows the TsAb, M22×H425× 520C9, and the BsAb, M22×520C9 were capable of inducing ADCC of SKBR-3 cells but the BsAb, M22×H425, was not. Various concentrations of antibodies were incubated with SKBR-3 cells and pre-activated PMNs.
Figure 17:
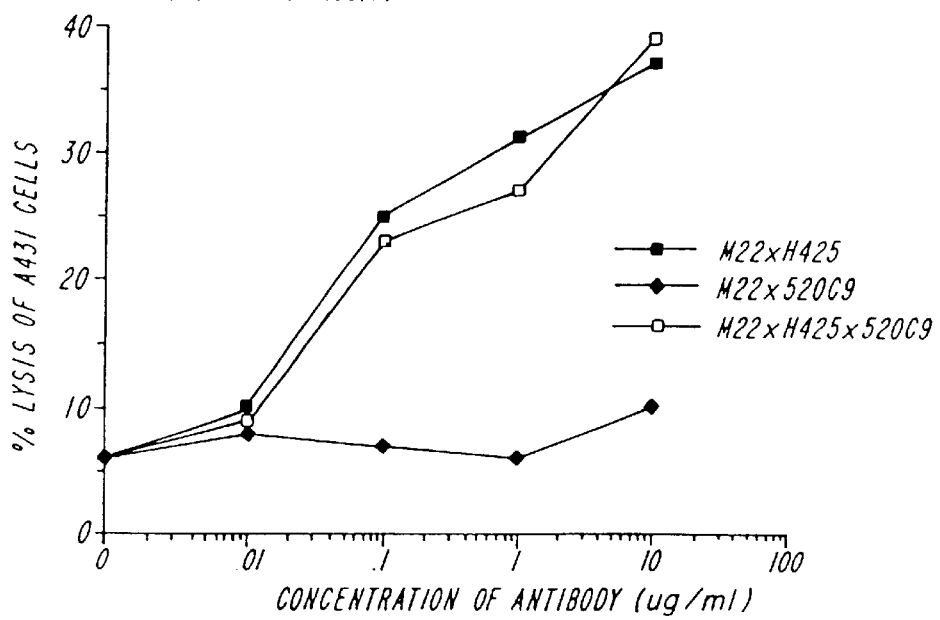
FIG. 17 is a graph that shows the TsAb, M22×H425× 520C9, and the BsAb, M22×H425 were capable of inducing ADCC of A431 cells but the BsAb, M22×520C9, was not. The assay was performed in a similar manner as the assay in FIG. 16.

The ability of the TsAb to mediate ADCC was analyzed using either SKBR-3 or A431 cells as targets. Human neutrophils cultured for 24–48 hours in the presence of IFN-γ and G-SF were used as effector cells. FIG. 16 demonstrates the both the BsAb, M22×520C9, and the TsAb, M22×H425×520C9, mediated lysis of SKBR-3 cells, whereas the BsAb, M22×H425, did not. On the other hand, FIG. 17 demonstrates the BsAb, M22×H425, and the TsAb, mediated lysis of SKBR-3 cells, whereas the BsAb, M22× 520C9, did not. These results demonstrated that the TsAb was capable of killing both HER2/neu and EGFR-overexpressing cells in the presence of $F_{c\gamma}RI$-expressing effector cells.

The trispecific antibody described above included M22, the murine version of the anti-FcγRI mAb. Such a trispecific antibody could be constructed using the single-sulfhydryl form of the humanized anti-FcγRI mAb, H22. The only difference being that single-sulfhydryl form is secreted as a F(ab')$_2$ fragment of this antibody. The single-sulfhydryl form is purified from culture supernatants utilizing ion exchange chromatography using Q-Sepharose followed by SP-Sepharose (Pharmacia, Piscataway, N.J.). Once the single-sulfhydryl form of H22 is purified, the creation of a trispecific antibody using this reagent would be identical to that described above using the F(ab')$_2$ fragment of M22.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A bispecific molecule capable of mediating antibody dependent cellular cytotoxicity comprising a humanized monoclonal antibody 22 or an antigen binding fragment thereof produced by a cell line having accession number CRL11177, and human epidermal growth factor.

2. A bispecific molecule capable of mediating antibody dependent cellular cytotoxicity comprising a humanized monoclonal antibody 22 or an antigen binding fragment thereof produced by a cell line having accession number CRL11177, and bombesin.

3. A bispecific molecule capable of mediating antibody dependent cellular cytotoxicity comprising a humanized monoclonal antibody 22 or an antigen binding fragment thereof produced by a cell line having accession number CRL11177, and heregulin.

4. The bispecific molecule of any one of claims 1–3, which is recombinantly produced.

5. The bispecific molecule of any one of claims 1–3, which is produced by genetically grafting ligand onto the constant region of the humanized monoclonal antibody 22.

6. A bispecific molecule capable of mediating antibody dependent cellular cytotoxicity comprising a humanized monoclonal antibody 22 or an antigen binding fragment thereof produced by a cell line having accession number CRL11177, and a humanized anti-epidermal growth factor receptor antibody.

7. A multispecific molecule capable of mediating antibody dependent cellular cytotoxicity comprising:

a portion which binds to an Fc receptor on an effector cell;

a portion which binds to HER 2/neu; and a portion which binds to an epidermal growth factor receptor (EGFR).

8. The multispecific molecule of claim 7, wherein the portion which binds to an Fc receptor on an effector cell is a monoclonal antibody 22 or an antigen binding fragment thereof produced by a hybridoma cell line having accession number HB-12147.

9. The multispecific molecule of claim 7, wherein the portion which binds to HER 2/neu is a monoclonal antibody (520C9) produced by a hybridoma cell line having ATCC accession number HB 8696, or an antigen binding fragment thereof.

10. The multispecific molecule of claim 7, wherein the portion which binds to an EGF receptor is a humanized anti-EGF receptor antibody.

11. The multispecific molecule of claim 7, wherein at least one of said binding portions is humanized.

12. The multispecific molecule of claim 7, wherein at least one of said binding portions comprises an antibody or a fragment thereof.

13. The multispecific molecule of claim 7, wherein the portion which binds to an Fc receptor on an effector cell binds to a site which is not bound by endogenous immunoglobulins.

14. The multispecific molecule of claim 13, wherein the Fc receptor is an Fcγ receptor.

15. The multispecific molecule of claim 14, wherein the Fcγ receptor is a FcγRI.

16. The multispecific molecule of claim 7, wherein the portion which binds to EGFR is an antibody.

17. The multispecific molecule of claim 7, wherein the portion which binds to HER 2/neu is an antibody.

* * * * *